United States Patent [19]

Kim et al.

[11] Patent Number: 5,561,146
[45] Date of Patent: Oct. 1, 1996

[54] MODIFIED GUANIDINO AND AMIDINO THROMBIN INHIBITORS

[75] Inventors: Kyoung S. Kim, Lawrenceville; Spencer D. Kimball, East Windsor; Jagabandhu Das, Mercerville; Edwin J. Iwanowicz, Cranbury, all of N.J.; Wen-Ching Han, Newtown, Pa.

[73] Assignee: Bristol-Myers Squibb Company, Princeton, N.J.

[21] Appl. No.: 323,336

[22] Filed: Oct. 14, 1994

Related U.S. Application Data

[63] Continuation-in-part of Ser. No. 257,995, Jun. 10, 1994.

[51] Int. Cl.$^6$ ............ A61K 31/445; C07D 207/09; C07D 211/26; C07D 211/60; C07D 401/12
[52] U.S. Cl. ............ 514/326; 514/183; 514/200; 514/212; 514/231.5; 514/233.8; 514/234.5; 514/235.2; 514/235.5; 514/235.8; 514/236.8; 514/237.2; 514/252; 514/256; 514/258; 514/266; 514/303; 514/314; 514/316; 514/318; 514/319; 514/321; 514/423; 548/530; 548/540; 540/200; 540/354; 540/480; 540/483; 540/544; 540/553; 540/597; 540/600; 540/603; 546/118; 546/152; 546/190; 546/193; 546/198; 546/208; 546/209; 546/210; 546/211; 546/212; 546/214; 544/121; 544/127; 544/128; 544/129; 544/130; 544/133; 544/135; 544/137; 544/139; 544/141; 544/238; 544/242; 544/277; 544/283; 544/236
[58] Field of Search ............ 540/200, 354, 540/480, 483, 544, 553, 597, 600, 603; 544/124, 141, 127, 238, 128, 242, 129, 277, 130, 283, 133, 236, 135, 137, 139; 546/118, 152, 208, 209, 190, 193, 198, 210, 211, 212, 214; 548/530, 540; 514/183, 252, 200, 256, 212, 258, 231.5, 266, 233.8, 303, 234.5, 314, 235.2, 316, 235.5, 318, 235.8, 321, 236.8, 326, 237.2, 423, 319

[56] References Cited

U.S. PATENT DOCUMENTS

| | | | |
|---|---|---|---|
| 4,161,522 | 7/1979 | Hamburger | 514/18 |
| 4,258,192 | 3/1981 | Okamoto et al. | 546/166 |
| 4,346,078 | 8/1982 | Bajusz et al. | 424/177 |
| 4,904,661 | 2/1990 | Pilgrim et al. | 514/237.5 |
| 5,002,964 | 3/1991 | Loscalzo | 514/423 |
| 5,217,705 | 6/1993 | Reno et al. | 424/1.1 |
| 5,264,420 | 11/1993 | Duggan | 514/19 |
| 5,354,738 | 10/1994 | Tjoeng | 514/19 |

FOREIGN PATENT DOCUMENTS

| | | |
|---|---|---|
| 0539204A1 | 4/1993 | European Pat. Off. |
| 0669317A1 | 3/1995 | European Pat. Off. |
| WO93/11152 | 6/1993 | WIPO |
| WO94/25049 | 11/1994 | WIPO |

OTHER PUBLICATIONS

Robert M. Knabb et al, "In Vivo Characterization of a New Synthetic Thrombin Inhibitor," Thrombosis and Hemostasis (1992) 67, 56–59.

Charles V. Jackson et al, "Pharmacological Assessment of the Antithrombotic Activity of the Peptide Thrombin Inhibitor, D-Methyl-Phenylalanyl-Prolyl-Arginal (GYKI-14766), in a Canine Model of Coronary Artery Thrombosis," J. Pharm. Exp. Ther. (1992) 261, 546–552.

Shauman et al. "Highly selective thrombin inhibitors" J. Med. Chem. 36 pp. 314–319 (1993).

Bajusz et al. "Highly selective and active anticoagulants" J. Med. Chem. 33 pp. 1729–1735 (1990).

Banner et al. "Serine protease:3D structure, mechanism of action and inhibitors" Prospect. Med. Chem. Verlag Publishing, Eds Testa Bernard, pp. 27–43 (1993).

Primary Examiner—Ceila Chang
Attorney, Agent, or Firm—Burton Rodney

[57] ABSTRACT

Thrombin inhibitors are provided which have the formula

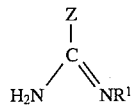

wherein Z is a thrombin inhibitor substructure containing distal and proximal binding site residues; and $R^1$ is cyano, hydroxyl, alkoxy, amino, aminoalkyl or nitro.

10 Claims, No Drawings

MODIFIED GUANIDINO AND AMIDINO THROMBIN INHIBITORS

REFERENCE TO OTHER APPLICATIONS

This is a continuation-in-part of U.S. application Ser. No. 257,995 filed Jun. 10, 1994.

FIELD OF THE INVENTION

The present invention relates to modified guanidino or modified amidino compounds which are thrombin inhibitors and thus useful in inhibiting formation of thrombin.

DESCRIPTION OF THE INVENTION

In accordance with the present invention, compounds having thrombin inhibitory activity are provided having the structure I $$H_2N-C(Z)=NR^1 \quad \text{I}$$

wherein Z is a thrombin inhibitor substructure containing residues binding at the distal and proximal sites (as described by Banner and Hadvary, J. Biol. Chem. (1991), 266, 20085–20093); and $R^1$ is cyano, hydroxyl, alkoxy, amino, aminoalkyl or nitro; including all stereoisomers thereof, and all pharmaceutically acceptable salts thereof.

It will be appreciated that the formula I structure includes all tautomers thereof, for example, $$H_2N-C(=Z)-NHR^1 \quad \text{or} \quad HN=C(ZH)-NHR^1.$$

Examples of the Z thrombin inhibitor substructure include (Z1)

$$R^5-NH-C(H)(R^4)-C(=O)-N(R^2)-CH(-(CH_2)_n-G)-R^3$$

(Z2)

$$R^{5'}-NH-C(H)(R^{4'})-C(=O)-NH-C(H)(-(CH_2)_t-NR-)-C(=O)-R^8, \text{ NH-C=O}$$

(Z3)

$$R^5-NH-C(H)(-(CH_2)_a-NR-)-C(=O)-N(R^9)-CH(-(CH_2)_n-)-R^3, R^2$$

Thus, the compounds of the invention include compounds of the structure

II $$R^5-NH-C(H)(R^4)-C(=O)-N(R^2)-CH(-(CH_2)_n-G-C(=NR^1)NH_2)-R^3$$

wherein G is an amido, sulfur or oxygen linking moiety including (G1): $-C(=O)-NH-CH_2-(CH_2)_m-CH_2-NR-$ (G2): $-C(=O)-NH-(CH_2)_p-A$ (G3): $-CH_2-X^1-CH_2-(CH_2)_m-CH_2-NR-$ (G4): $-CH_2-X^1-(CH_2)_p-A$ including all stereoisomers thereof; and including all pharmaceutically acceptable salts thereof; wherein n is 0, 1 or 2; and the lower bond connects with $$-C(=NR^1)NH_2.$$

$R^2$ and $R^3$ are independently hydrogen, lower alkyl, cycloalkyl, aryl, hydroxy, alkoxy, oxo, thioketal, thioalkyl, thioaryl, amino or alkylamino; or $R^2$ and $R^3$ together with the carbons to which they are attached form a cycloalkyl, aryl, or heteroaryl ring;

$R^4$ is hydrogen, hydroxyalkyl, hydroxy(alkyl)alkyl, aminoalkyl, alkyl, cycloalkyl, aryl, arylalkyl, alkenyl, alkynyl, amidoalkyl, arylalkoxyalkyl, or an amino acid side chain, either protected or unprotected; and $R^5$ is $$R^6-S(=O)_2-$$

where $R^6$ is lower alkyl, aryl, arylalkyl, cycloheteroalkyl, heteroaryl, quinolinyl or tetrahydroquinolinyl; or $R^5$ is hydrogen, $$-C(=O)-R^7,$$

$-CO_2R^7$ or $-CONHR^7$ (wherein $R^7$ is lower alkyl, aryl, arylalkyl, cycloheteroalkyl or heteroaryl). $R^5$ can also be $R^{7'}O_2C$-alkyl-,

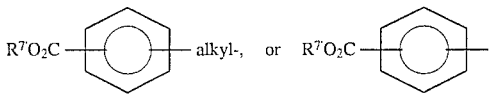

(wherein R[7'] is H, alkyl, aryl, arylalkyl, cycloheteroalkyl or heteroalkyl).

In compounds of structure II where G is the amido moiety (G1), that is

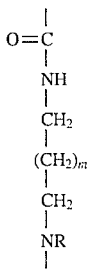

m is 0, 1, 2, 3 or 4; and R is H or alkyl.

In compounds of structure II where G is the amido moiety (G2), that is

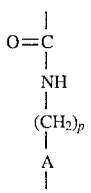

p is 0, 1 or 2.

In compounds of structure II where G is (G3), that is

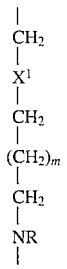

$X^1$ is NHCO, S, SO, $SO_2$ or O;
m is 0, 1, 2, 3, 4; and R is H or alkyl.

In compounds of structure II where G is (G4), that is

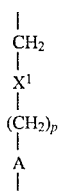

$X^1$ and p are as defined above.

In the above structures A is aryl or cycloalkyl, or an azacycloalkyl ring A1 of 3 to 7 carbons in the ring or an azacycloheteroalkyl ring A2 of 4 to 6 carbons in the ring, A1 or A2

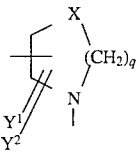

where X is $CH_2$ (to provide A1) or X is O or S (to provide A2);

q is 0, 1, 2, 3 or 4 if X is $CH_2$;

q is 2, 3 or 4 if X is O or S;

$Y^1$ and $Y^2$ are independently H, lower alkyl, halo or keto; and provided that where X is a hetero atom (that is, A is azacycloheteroalkyl (A2)), then there must be at least a 2-carbon chain between X and any N atom in the ring A2 or outside ring A2.

In addition, compounds of the invention I include compounds having the structure III

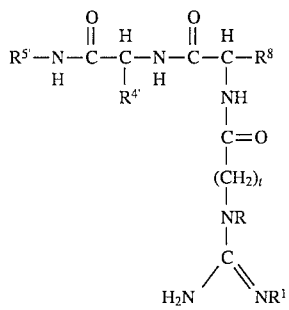

wherein $R^{5'}$ is

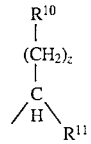

where z is 0, 1 or 2;

$R^{10}$ is H, alkyl, cycloalkyl, aryl, cycloheteroalkyl or heteroaryl;

$R^{11}$ is H, alkyl, $CO_2R^c$ or $CONR^aR^b$;

wherein $R^c$ is H or alkyl; and $R^a$ and $R^b$ are independently selected from H, alkyl, cycloalkyl, cycloheteroalkyl, aryl, or heteroaryl;

$R^{4'}$ is an amino acid side chain;

t is 2, 3, 4 or 5;

R is H, or lower alkyl; and $R^8$ is $(CH_2)_y$—$R^{12}$, where y is 0, 1 or 2 and $R^{12}$ is cycloalkyl; heteroaryl; $CO_2H$; $CONR^aR^b$; or aryl optionally substituted with $NO_2$, OH, alkoxy, acyloxy,

halogen, alkyl, aryl, $CO_2$alkyl, CONHalkyl, alkylthio, arylthio, NHalkyl or NHcycloalkyl.

In addition, compounds of the invention I include compounds having the structure IV

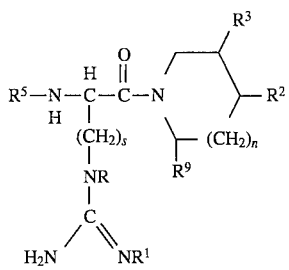

wherein s is 2, 3 or 4, and n, $R^5$, $R^2$, $R^3$, R and $R^1$ are as defined above, and $R^9$ is H or $CO_2R^{16}$ where $R^{16}$ is H or alkyl.

All of the compounds of the invention I, II, III and IV include all stereoisomers thereof and pharmaceutically acceptable salts thereof.

Examples of the A1 or A2 rings (azacycloalkyl, or azacycloheteroalkyl) which may be employed herein include

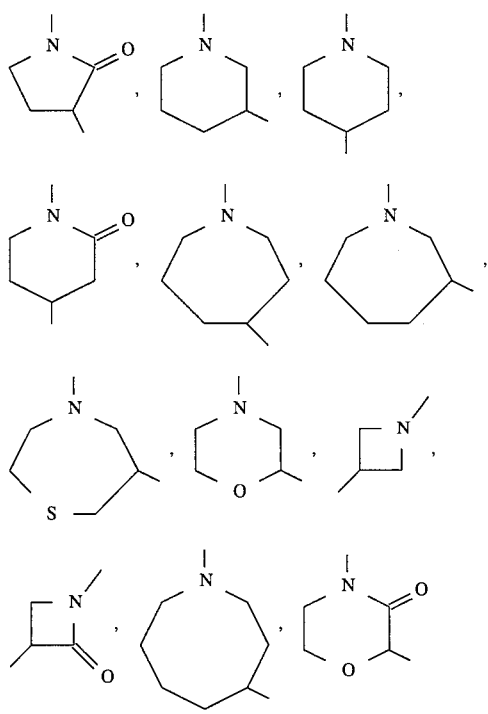

and the like wherein the N— is connected to

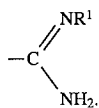

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents (for example, to form $CF_3$ or $CF_3CH_2$) and/or 1 or 2 of the following substituents: an aryl substituent (for example, to form benzyl or phenethyl), an alkyl-aryl substituent, a haloaryl substituent, a cyclo-alkyl substituent, an alkylcycloalkyl substituent, an alkenyl substituent, an alkynyl substituent, hydroxy or a carboxy substituent. It will be appreciated that the same "alkyl" group may be substituted with one or more of any of the above substituents.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy groups.

The term "aryl" or "Ar" as employed herein by itself or as part of another group refers to monocyclic or bicyclic aromatic groups containing from 6 to 10 carbons in the ring portion, such as phenyl, or naphthyl. Aryl (or Ar), phenyl or naphthyl may include substituted aryl, substituted phenyl or substituted naphthyl, which may include 1 or 2 substituents on either the Ar, phenyl or naphthyl such as lower alkyl, cyano, amino, alkylamino, dialkylamino, nitro, carboxy, carboalkoxy, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or aralkoxy" includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

The term "lower alkenyl" or "alkenyl" as employed herein by itself or as part of another group includes a carbon chain of up to 16 carbons, preferably 3 to 10 carbons, containing one double bond which will be separated from "N" by at least one saturated carbon moiety such as —$(CH_2)_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein by itself or as part of another group includes a carbon chain of up to 16 carbons, preferably 3 to 10 carbons, containing one triple bond which will be separated from "N" by at least one saturated carbon moiety such as —$(CH2)_{q'}$— where q' can be 1 to 14, such as 2-propynyl, 2-butynyl, 3-butynyl and the like.

The term "heteroaryl" or heteroaromatic by itself or as part of another group refers to a 5- to 12-membered aromatic ring, preferably 5- or 6-membered aromatic ring, which includes 1 or 2 hetero atoms such as nitrogen, oxygen or sulfur, such as

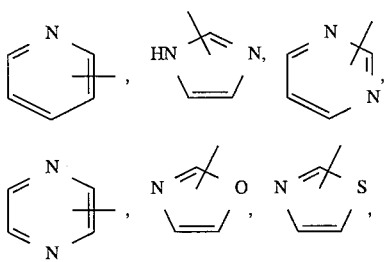

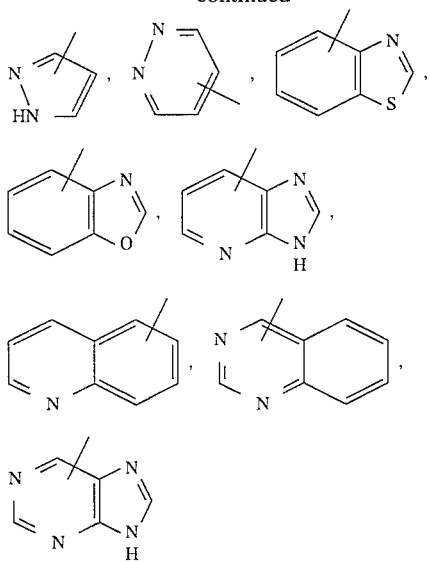

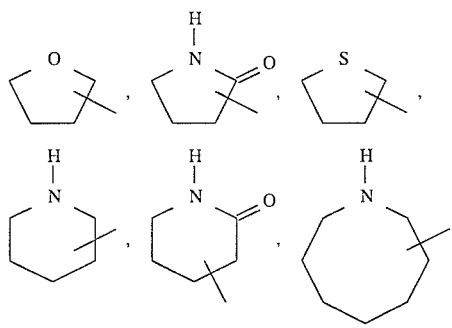

and the like. The heteroaryl rings may optionally be fused to aryl rings defined previously. The heteroaryl rings may optionally include 1 or 2 substituents such as halogen (Cl, Br, F or $CF_3$), lower alkyl, lower alkoxy, carboxy, amino, lower alkylamino and/or dilower alkylamino.

The term "cycloheteroalkyl" as used herein refers to a 5-, 6- or 7-membered saturated ring which includes 1 or 2 hereto atoms such as nitrogen, oxygen and/or sulfur, such as and the like.

The term "cycloheteroalkylalkyl" refers to a 5-, 6- or 7-membered saturated ring which includes 1 or 2 heteroatoms such as nitrogen, oxygen or sulfur, such as any of the cycloheteroalkyl rings as disclosed above, linked to a $(CH_2)_x$ chain wherein x is 1 to 12, preferably 1 to 8.

The term "amino acid side chain" refers to the side chain of any of the known alpha-amino acids such as the side chain of each of arginine, histidine, alanine, glycine, lysine, glutamine, leucine, valine, serine, homoserine, allothreonine, naphthylalanine, isoleucine, phenylalanine and the like.

Preferred are compounds of formula I wherein Z is (Z1) and G is (G2)

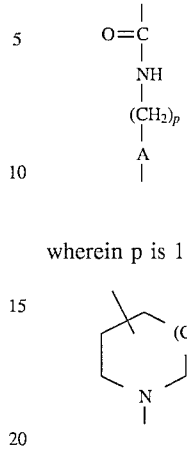

wherein p is 1 or 2, A is an azacycloalkyl ring

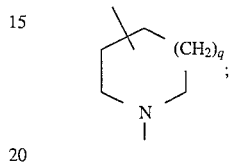

where q is 0 or 1; and
$R^1$ is OH, $NH_2$, CN or alkoxy;
$R^5$ is lower alkyl$SO_2$, arylalkyl$SO_2$, H or $HO_2C$-alkyl-;
$R^4$ is aralkyl or hydroxyalkyl;
$R^2$ and $R^3$ are each H;
n is 0 or 1.

A more preferred embodiment of the heterocyclic thrombin inhibitors of the invention has the structure IA

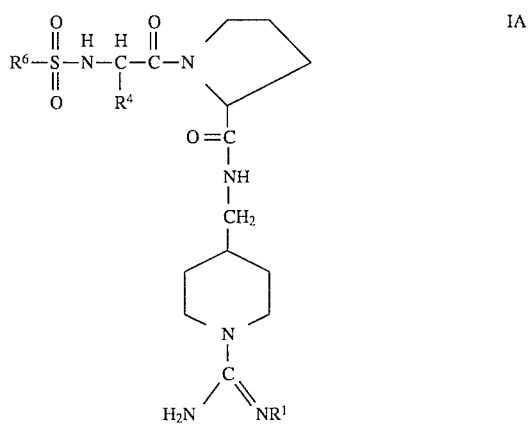

where $R^4$ is aralkyl (preferably benzyl), aryl (preferably phenyl), or arylalkoxyalkyl (preferably benzyloxymethyl) and $R^6$ is alkyl (preferably methyl, ethyl, trifluoro ethyl or propyl) or arylalkyl (preferably benzyl) and $R^1$ is OH or $NH_2$, including all stereoisomers thereof.

Other preferred compounds of formula I are those wherein Z is (Z1), G is G1, n is 0 or 1; p is 2; $R^5$ is aryl$SO_2$- or alkyl$SO_2$- or $HO_2C$-alkyl-; $R^4$ is arylalkyl or hydroxyalkyl such as hydroxymethyl; $R^2$ is hydrogen or lower alkyl such as methyl or ethyl; $R^3$ is H; and compounds of formula IB:

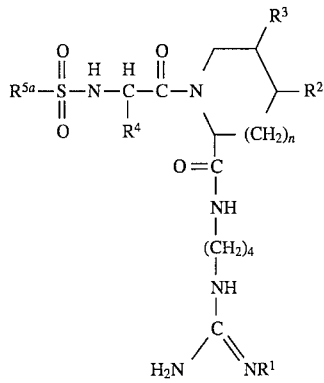

IB

R⁴ = HOCH₂—, HOCH(alkyl)-

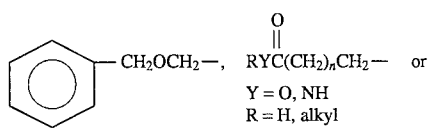

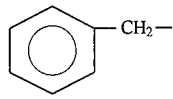

R⁵ᵃ = aryl, alkyl or arylalkyl
R¹ = NH₂, OH

Other compounds preferred are compounds of formula I wherein z is (Z1) and G is (G3) wherein X¹ is S or SO₂, n is 0, p is 1, m is 2 and R¹ is OH or NH₂; R² and R³ are each H, R⁴ is H or —CH₂OH, and R⁵ is

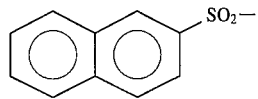

or HO₂C-alkyl-.

Other preferred compounds are compounds of formula I wherein Z is (Z1) and G is (G4), R¹ is CN, NH₂, OH or OCH₃; R² and R³ are each H, p is 1, A is azacycloalkyl, R⁴ is hydroxymethyl or benzyl and R⁵ is

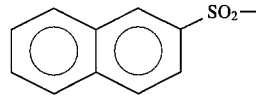

H, BOC or CBZ.

Preferred compounds of formula I wherein Z is (Z2) are compounds wherein t is 2, 3, 4 or 5, z is 0 or 1; $R^{4'}$ is optionally substituted phenyl, alkyl, hydroxyalkyl or aminocarbonylalkyl; $R^{12}$ is cycloalkyl, phenyl or H; y is 0, 1 or 2; $R^{11}$ is alkoxycarbonyl or alkyl; $R^{10}$ is aryl or cycloalkyl; and R¹ is OH, NH₂, CN or OCH₃.

More preferred compounds of formula I wherein z is (Z2) are compounds wherein p is 1; z is 1; y is 1; $R^{12}$ is p-NO₂C₆H₅, -o-FC₆H₅, or C₆H₅;

$R^{4'}$ is

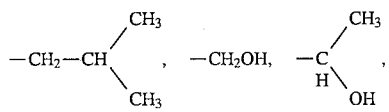

R¹⁰ is C₆H₅, or

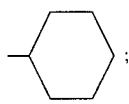

R¹¹ is HOCH₂— or alkyl.
R¹ is CN, OH, NH₂, or OCH₃; R is H.

Preferred compound of formula I wherein Z is (Z3) are compounds wherein R⁵ is heteroarylsulfonyl, such as

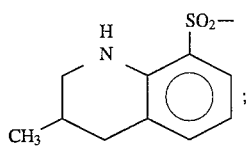

R² and R³ are each H, R⁹ is CO₂alkyl, n is 1, p is 3, R is H and R¹ is CN, OH, NH₂, or OCH₃.

The compounds of formula I of the invention may be prepared according to the following reaction sequences.

The compounds of formula I of the invention wherein Z is (Z1) and G is (G1) that is

I'

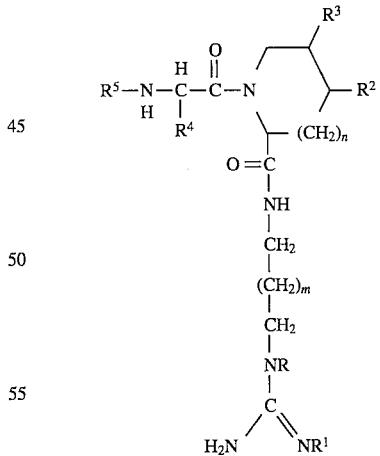

may be prepared according to the following Reaction Sequence I.

Reaction Sequence I

A. $R^5 \neq H$

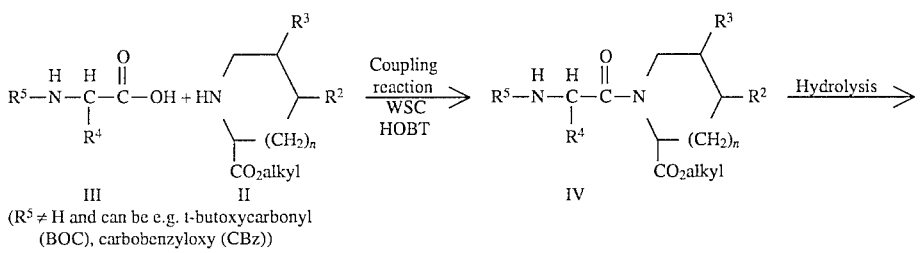

III
($R^5 \neq H$ and can be e.g. t-butoxycarbonyl (BOC), carbobenzyloxy (CBz))

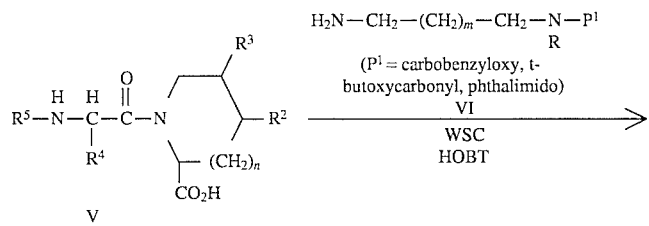

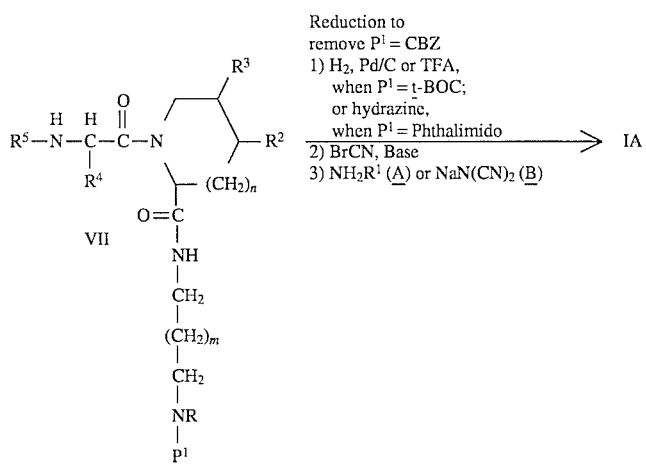

B. $R^5 = H$

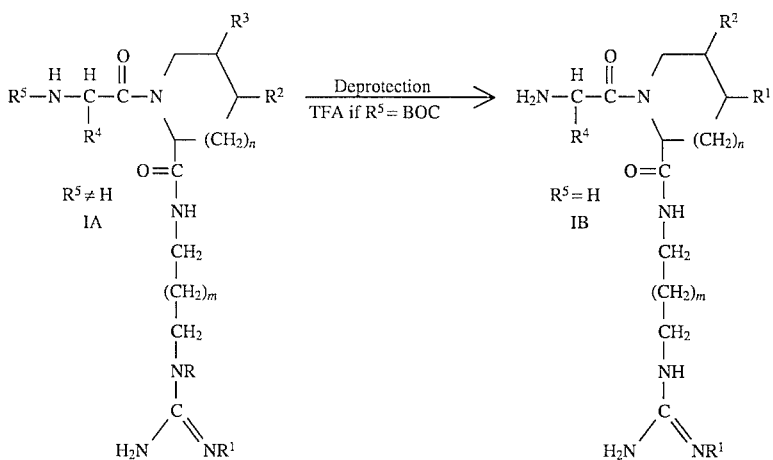

As seen in the above Reaction Sequence I, compounds of formula I are prepared as follows. The ester II is made to undergo a carbodiimide coupling reaction with protected amino acid III in the presence of ethyl 3-(3-dimethylamino)propyl carbodiimide hydrochloride (WSC) or dicyclohexylcarbodiimide (DCC), and 1-hydroxybenzo-triazole monohydrate (HOBT), and N-methylmorpholine (NMM), and in the presence of an inert organic solvent such as dimethylformamide (DMF), THF or N-methylpyrrolidone, to form the amide IV. Amide IV is hydrolyzed by treatment with alkali metal base such as NaOH or LiOH in the presence of an alcohol solvent such as methanol or ethanol. The reaction mixture is acidified with HCl, $KHSO_4$ or $H_2SO_4$, to form acid V. The acid V is then subjected to a carbodiimide coupling reaction wherein V is treated with protected amine VI in the presence of WSC or DCC, and HOBT, and NMM, in the presence of an inert organic solvent such as dimethylformamide, THF or N-methylpyrrolidone, to form amide VII. The amide VII is then dissolved in an alcohol solvent such as ethanol or methanol, to which HCl has been added and the mixture is hydrogenated over Pd—C or Pd(OH)$_2$—C in the case where P$^1$ is carbobenzyloxy. The crude material is separated by conventional procedures and the desired isomers are treated with cyanogen bromide and base, followed by amine A or cyanide E in the presence of an alcohol solvent such as methanol or ethanol to form the compound of the invention IA where R$^5$≠H.

Compounds of the invention where R$^5$ is H may be formed by deprotecting IA by treatment with trifluoroacetic acid (TFA) when R$^5$ is t-butoxycarbonyl (BOC) or H$_2$—Pd/C when R$^5$ is carbobenzyloxy (CBz), with or without the presence of dry inert organic solvent such as dichloromethane, chloroform or THF, at temperatures within the range of from about −15° to about 20° C., to form IB.

The compounds of formula I of the invention where Z is (Z1) and G is (G2)

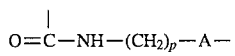

wherein A is azacycloalkyl or azacycloheteroalkyl, may be prepared according to the following Reaction Sequence II:

Reaction Sequence II

A. where R$^5$ ≠ H

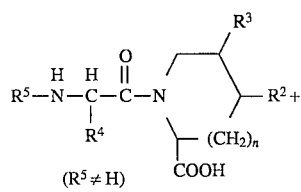

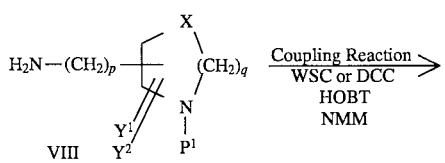

(where P$^1$ is a protecting group such as BOC or CBz)

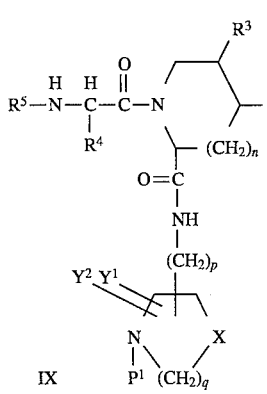

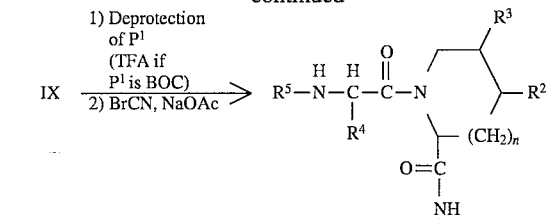

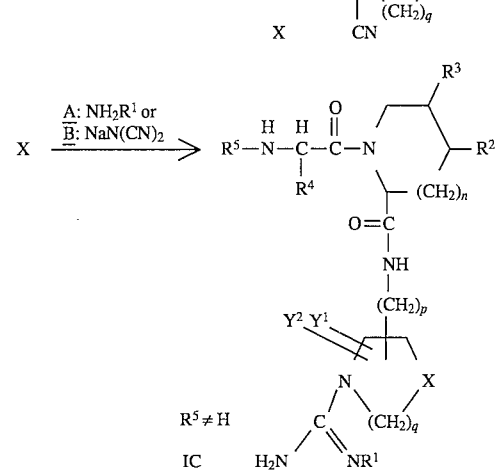

B. where R$^5$ = H

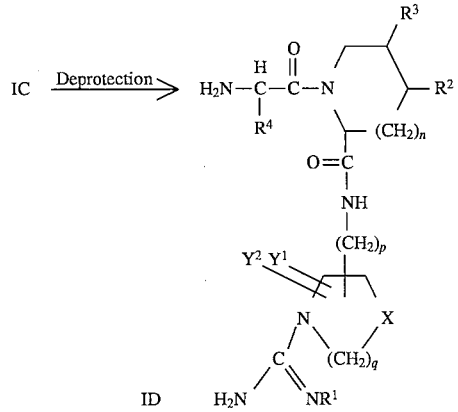

As seen in the above Reaction Sequence II, compounds of formula I wherein Z is (Z1) and G is (G2), that is

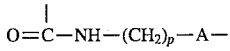

and A is azacycloalkyl or azaheteroalkyl, are prepared as follows. The protected acid V is made to undergo a carbodiimide coupling reaction with amine VIII in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide IX. Amide IX is deprotected by treatment with, for example, H$_2$/Pd—C, if P$^1$ is CBz, and is then treated with cyanogen bromide to form Compound x. Compound X is treated with amine A or cyanide B in the presence of alcohol solvent, such as ethanol to form amine IC of the invention where $R^5 \neq H$.

Compounds of the invention ID where $R^5$ is H are prepared by deprotection of IC by treatment with trifluoroacetic acid (if P=BOC), with or without the presence of dry inert organic solvent such as dichloromethane, chloroform or THF, at temperatures within the range of from about −15° to about 20° C.

The starting materials of formula VIII are known in the art or may be prepared by those skilled in the art employing conventional techniques.

The compounds of formulae I and IA of the invention where Z is (Z1) and G is (G2) that is

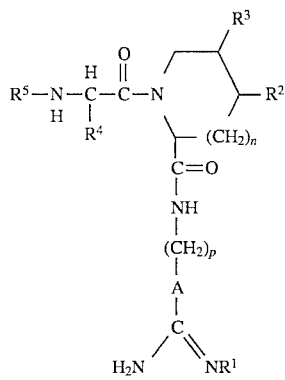

where A is aryl or cycloalkyl may be prepared according to the following Reaction Sequence III:

Reaction Sequence III

A. $R^5 \neq H$

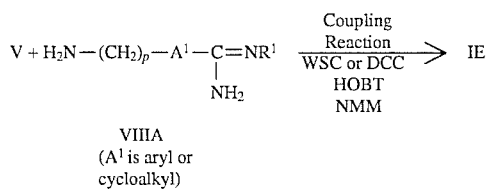

VIIIA
($A^1$ is aryl or cycloalkyl)

B. $R^5$ = H

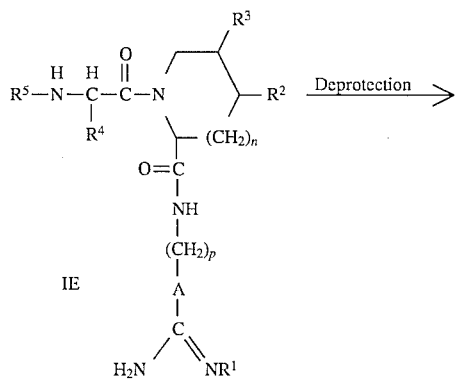

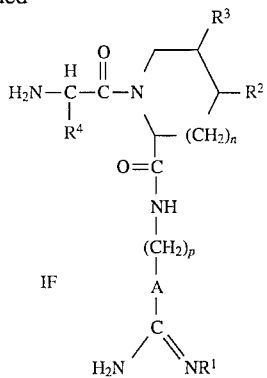

As seen in Reaction Sequence III, compounds of formulae I and I″ where G is

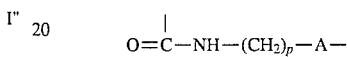

are prepared as follows. The protected acid V is subjected to a carbodiimide coupling reaction wherein V is treated with protected amine VIIIA in the presence of WSC or DCC, and HOBT, and NMM, in the presence of an inert organic solvent such as dimethylformamide, THF or N-methylpyrrolidone, to form amide of the invention IE where $R^5 \neq H$. The amide IE may be dissolved in an alcohol solvent such as ethanol or methanol, to which HCl has been added and the mixture is hydrogenated over Pd—C or Pd(OH)$_2$—C, in the case where $R^5$ is carbobenzyloxy, to form compounds of the invention IF where $R^5$ is H.

The starting compound VIIIA is known in the art or may be prepared employing conventional procedures.

The starting acid V may be prepared from ester IV by hydrolyzing ester IV by treating with a base such as NaOH, KOH or LiOH and then neutralizing the resulting alkali metal salt with strong acid such as HCl or oxalic acid.

The compounds of formula I of the invention where Z is (Z1) and G is (G3) —CH$_2$—X$^1$—(CH$_2$)$_m$—CH$_2$NR— wherein X$^1$ is S, SO, or SO$_2$, that is

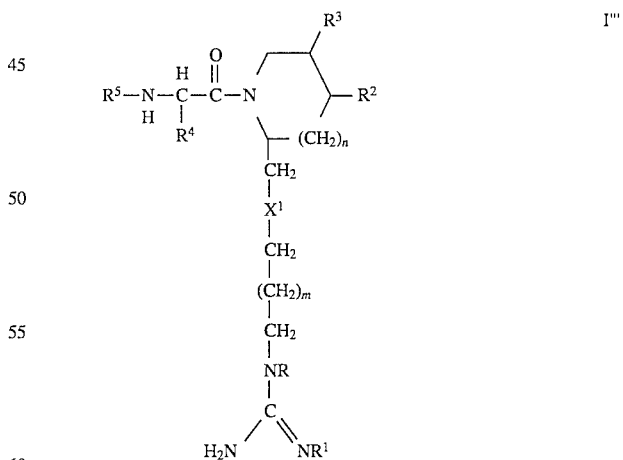

may be prepared according to the Reaction Sequence IV

Reaction Sequence IV

A. where $R^5 \neq H$:

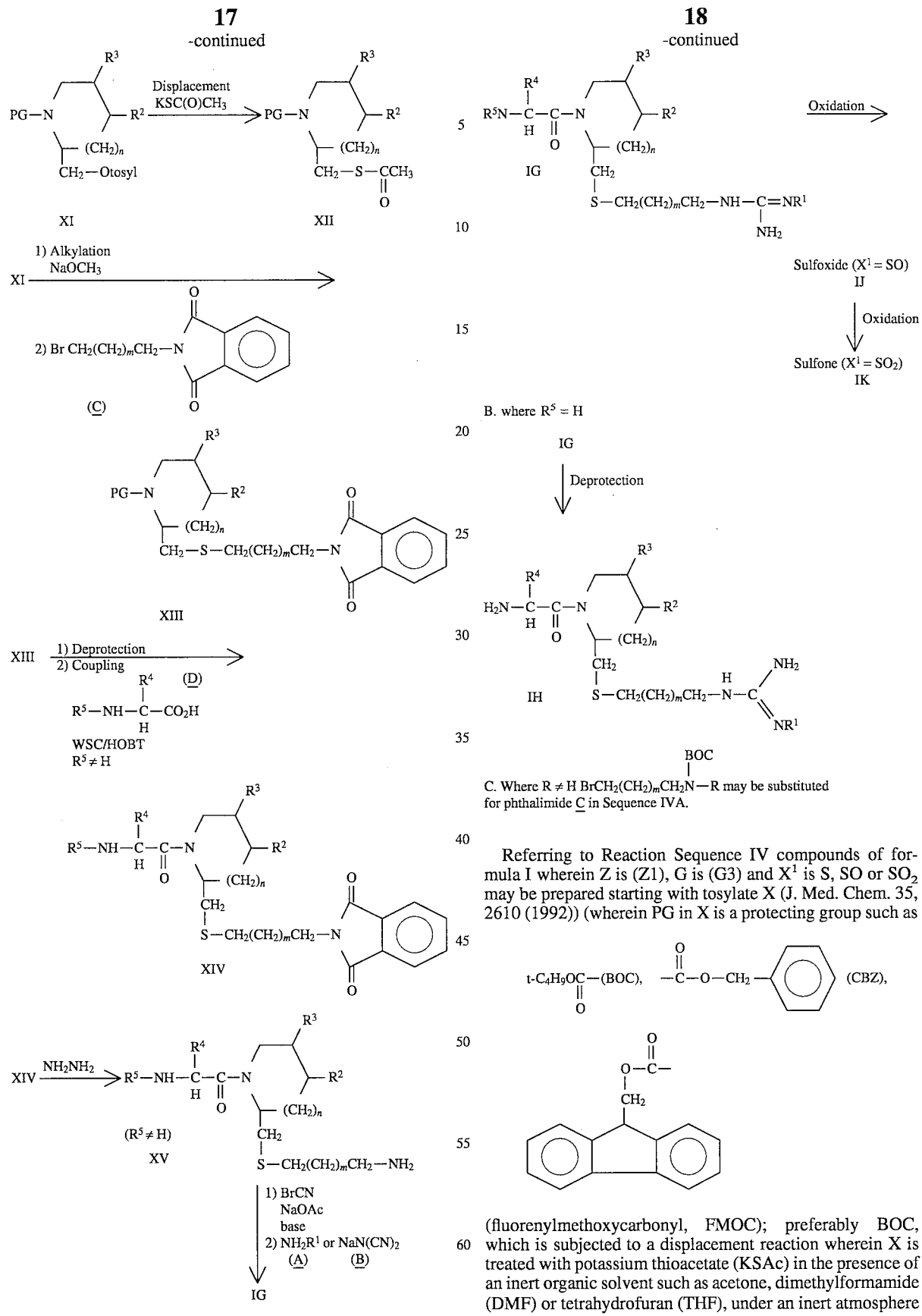

Referring to Reaction Sequence IV compounds of formula I wherein Z is (Z1), G is (G3) and $X^1$ is S, SO or $SO_2$ may be prepared starting with tosylate X (J. Med. Chem. 35, 2610 (1992)) (wherein PG in X is a protecting group such as t-$C_4H_9OC$—(BOC), —C(=O)—O—$CH_2$—Ph (CBZ), (fluorenylmethoxycarbonyl, FMOC); preferably BOC, which is subjected to a displacement reaction wherein X is treated with potassium thioacetate (KSAc) in the presence of an inert organic solvent such as acetone, dimethylformamide (DMF) or tetrahydrofuran (THF), under an inert atmosphere such as argon, at a temperature within the range of from about 0° to about 100° C. to form thioacetate XII. Thioacetate XII is then alkylated by reacting XII with an alkali metal alkoxide such as sodium methoxide or potassium t-butoxide in an inert organic solvent such as THF, DMF or diethylether, in the presence of an alcohol solvent such as methanol or ethanol under an inert atmosphere such as argon, at a temperature within the range of from about −30° to about 50° C. To the resulting solution is added N-bromoalkyl-phthalimide C to form the thiophthalimide XIII. Thiophthalimide XII is deprotected by treatment with a deprotecting agent such as trifluoroacetic acid where PG is BOC or HBr/acetic acid where PG is CBZ, with or without the presence of dry inert organic solvent such as dichloromethane, chloroform or THF, to form a crude amine salt XIIIA.

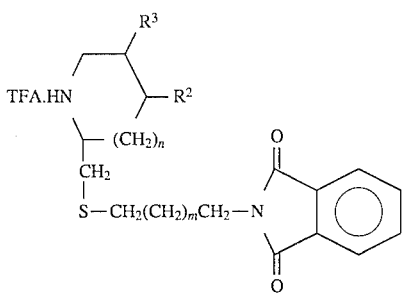

XIIIA

The resulting salt XIIIA is made to undergo a carbodiimide coupling reaction with protected amino acid D

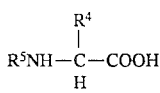

D (wherein $R^5$ serves as a protecting group) in the presence of 1-hydroxybenzotriazole monohydrate (HOBT), ethyl-3-(3-dimethylamino)propyl carbodiimide (WSC) or dicyclohexylcarbodiimide (DCC), and N-methylmorpholine (NMM), in the presence of an inert organic solvent such as dimethylformamide (DMF), THF or N-methyl-pyrrolidone, to form XIV.

XIV is then reacted with anhydrous hydrazine in the presence of dry solvent such as dichloromethane, chloroform or THF, and an alcohol solvent such as methanol or ethanol, to form thioalkylamine compound XV. Compound XV is then reacted with cyanogen bromide and then with amine A or cyanide B, as described hereinbefore, to form compound of the invention IG.

Compound IG may be oxidized to the corresponding sulfoxide IJ or to the corresponding sulfone IK.

The oxidation is carried out with an oxidizing agent such as m-chloroperbenzoic acid (MCPBA), oxone or sodium periodate in the presence of an inert organic solvent such as dichloromethane, employing from about 0.9 to about 1.5 moles of oxidizing agent per mole of amide, to form the corresponding sulfoxide. The corresponding sulfone may be formed employing from about 2 to about 3 moles of oxidizing agent per mole of amide.

Compounds of formula IG of the invention where $R^5$ is H are prepared by deprotecting IG as described hereinbefore, to form IH where $R^5$ is H.

The compounds of the Formula I of the invention where Z is (Z1) and G is (G4) —$CH_2$—$X^1$—$(CH_2)_p$—A— wherein $X^1$ is S, SO, or $SO_2$ and A is azacycloalkyl or azacycloheteroalkyl may be prepared according to Reaction Sequence V.

Reaction Sequence V

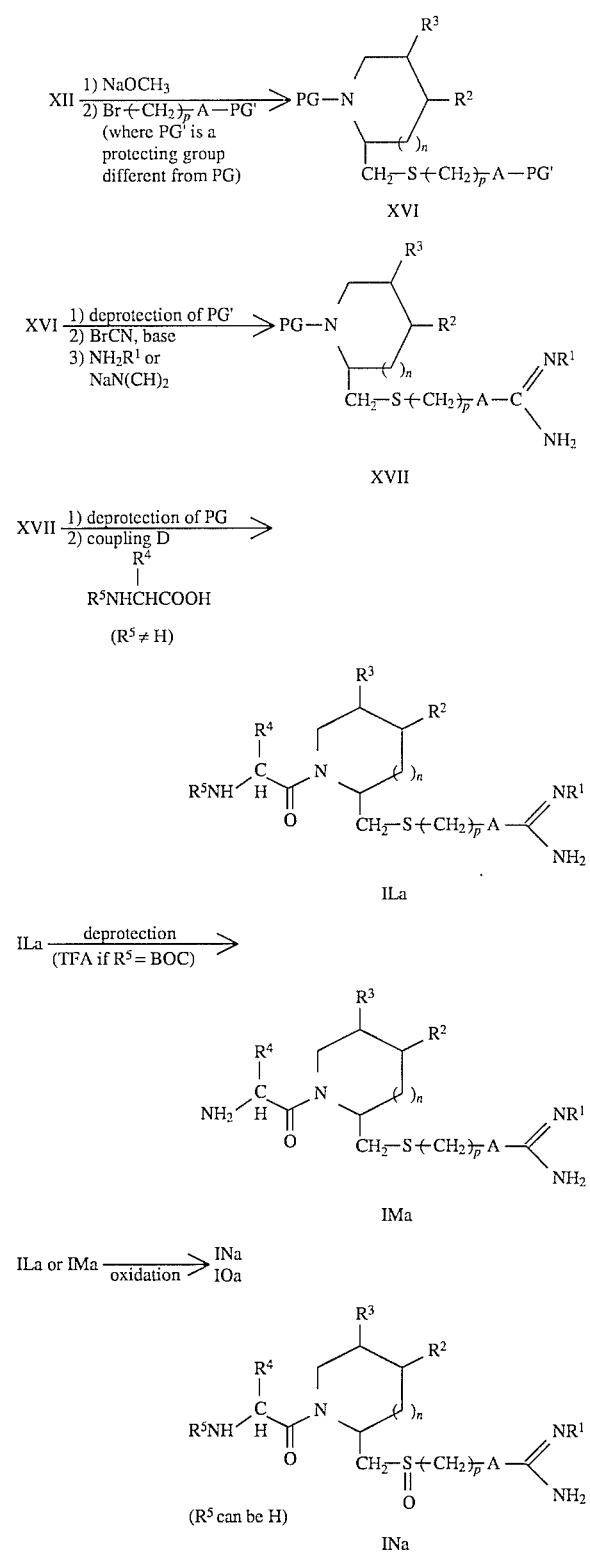

-continued

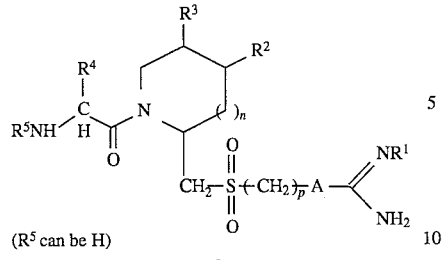

(R⁵ can be H)

IOa

The compounds of the Formula I of the invention where Z is (Z1) and G is (G4) —CH₂—X¹—(CH₂)$_p$—A— wherein X¹ is S, SO, or SO₂ and A is aryl or cycloalkyl may be prepared according to Reaction Sequence VI.

Reaction Sequence VI

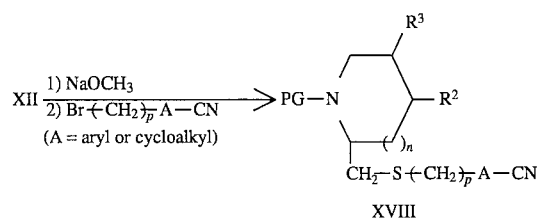

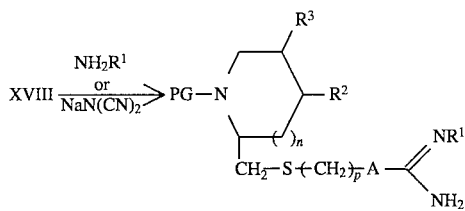

XIX $\xrightarrow[\text{2) coupling of } \underline{C}]{\text{1) deprotection of PG}}$

R⁵NHCHCOOH
|
R⁴

(R⁵ ≠ H)

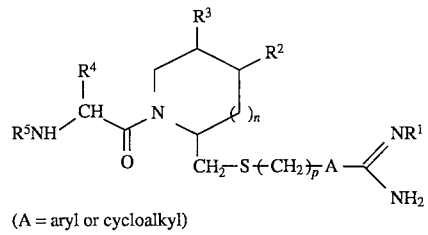

(A = aryl or cycloalkyl)
ILb

↓ deprotection
(TFA if R⁵ = BOC)

-continued

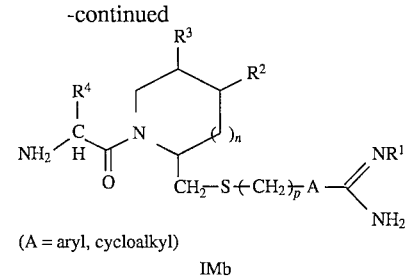

(A = aryl, cycloalkyl)
IMb

ILb or IMb $\xrightarrow{\text{oxidation}}$ INb
                                    IOb

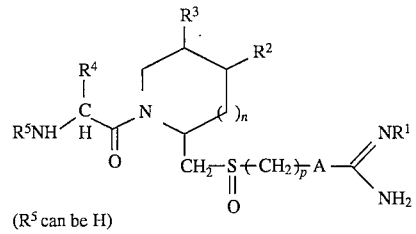

(R⁵ can be H)
INb

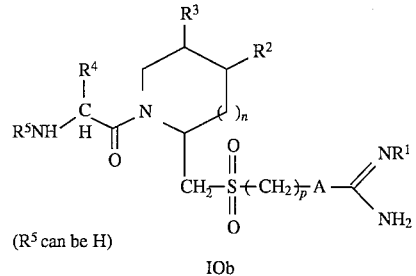

(R⁵ can be H)
IOb

The compounds of Formula I of the invention where Z is (Z1) and G is (G4) —CH₂—X¹—(CH₂)$_p$—A— wherein X¹ is O may be prepared according to Reaction Sequence VII.

Reaction Sequence VII (Preparation of I Where X¹ is Oxygen)

Reaction Sequence VII (Preparation of I where X¹ is oxygen)

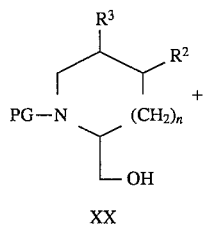

XX

MsO—W
XXI $\xrightarrow[\text{Xylene}]{\text{KOH}}$ where W is
—CH₂—(CH₂)$_m$—CH₂NRPG' or
—(CH₂)$_p$—A—CN (A = aryl, cycloakyl) or
—(CH₂)$_p$—A—PG' (A = azacycloalkyl, azacycloheteroalkyl)

-continued
Reaction Sequence VII (Preparation of I where $X^1$ is oxygen)

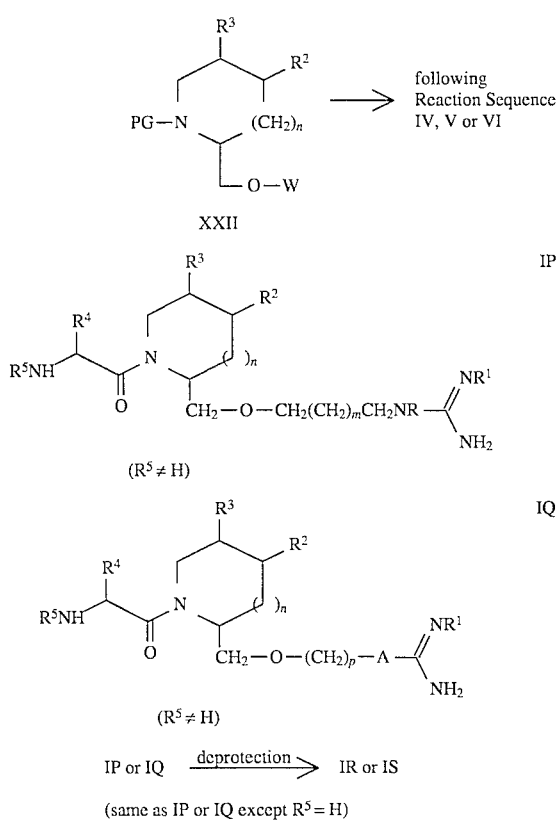

IP or IQ $\xrightarrow{\text{deprotection}}$ IR or IS (same as IP or IQ except $R^5$ = H)

Referring to Reaction Sequence V, compounds of formula I of the invention wherein Z is (Z1), G is (G4) and A is azacycloalkyl or azacycloheteroalkyl may be prepared by treating XII with an alkali metal alkoxide followed by a compound of formula $Br(CH_2)_p$—A—PG' where PG' is a protecting group different from PG, to give XVI. Compounds ILa, IMa, INa and IOa are prepared using the steps described in Reaction Sequence IV.

Referring to Reaction Sequence VI, compounds of formula I of the invention where Z is (Z1), G is (G4) and A is aryl or cycloalkyl may be prepared by reacting XII with an alkali metal alkoxide followed by a compound of formula Br—$(CH_2)_p$—A—CN to give XVIII. Compounds ILb, IMb, INb, and IOb are prepared using the steps described previously.

The key step for the preparation of compounds wherein $X^1$ is oxygen is shown in Scheme VII. Treatment of the protected alcohol XX with KOH and a mesylate (Ms) of formula XXI in xylene (J. Med. Chem 1986, 29, 2335–2347) will provide the series of compounds XXII. Further steps in the preparation of compounds of formula I wherein $X^1$ is oxygen may be effected in analogy with the previously described Schemes to form compounds IP, IQ, IR and IS of the invention.

The compounds of formula I of the invention where Z is (Z1) and G is (G3) or (G4) and $X^1$ is NHCO that is

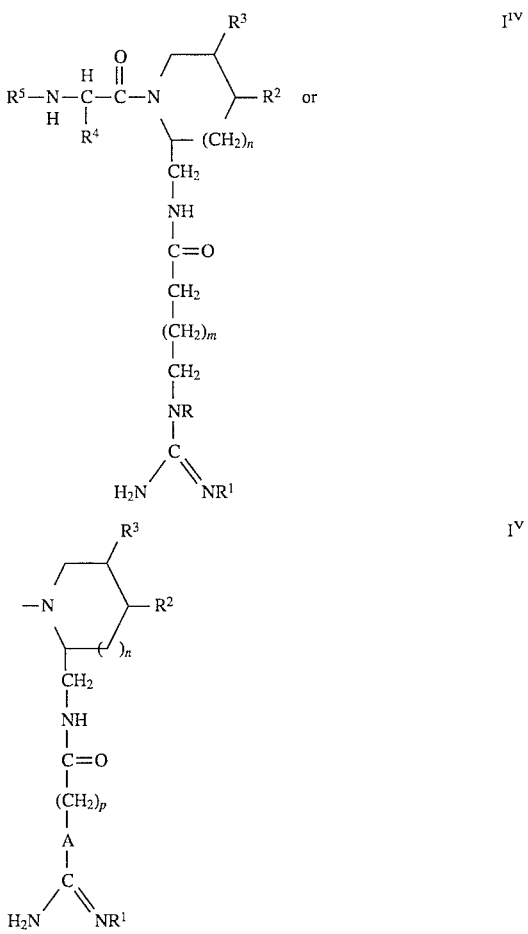

may be prepared according to the following Reaction Sequence VIII.

Reaction Sequence VIII

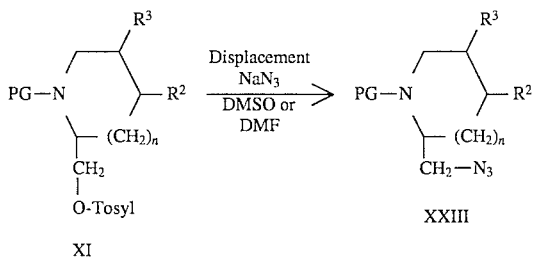

-continued
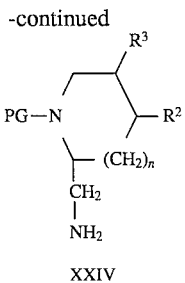
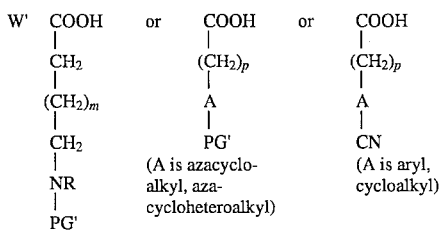
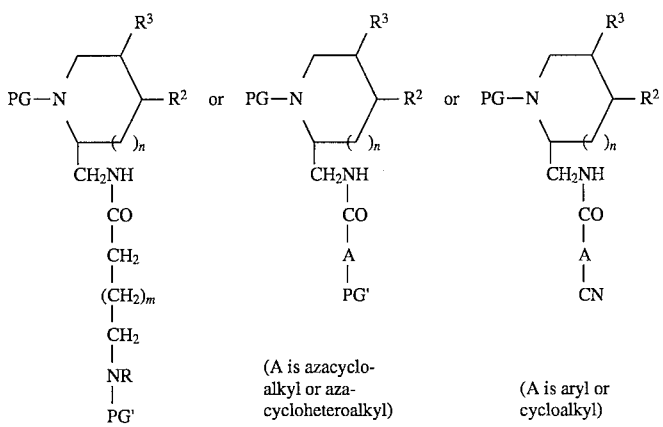
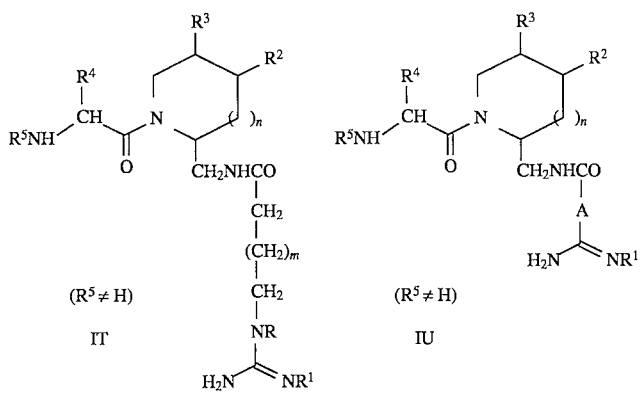
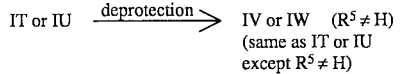
As seen in Reaction Sequence VIII, compounds of Formula I of the invention wherein Z is (Z1) and G is (G3) or (G4) and $X^1$ is —NHCO— are prepared as follows. Tosylate XI is made to undergo a displacement reaction with sodium azide in the presence of an inert organic solvent such as dimethylsulfoxide (DMSO) or dimethylformamide (DMF), at a temperature within the range of from about 50° to about 90° C., to form azide XXXIII which is reduced by reaction with a reducing agent such as H$_2$/Pd—C or triphenylphosphine/H$_2$O, lithium aluminum hydride (LAH) or stannous chloride, to form the corresponding amine XXIV.

The amine XXIV is made to undergo a coupling reaction with a compound W'COOH of formula XXV to give a compound of formula XXVI (G is (G3)), or XXVII (G is (G4) and A is azacycloalkyl or azacycloheteroalkyl, or XXVIII (G is (G4) and A is aryl or cycloalkyl). The compound of formula XXVI may be converted into a compound of the invention of formula IT by previously described methods. Compounds of formula XXVII or XXVIII may be converted into a compound of formula IU by previously described methods. Both IV and IW (R$^5$=H) may be prepared from compounds of formula IT or IU by removal of R$^5$ where R$^5$ is a protecting group.

The compounds of formula I of the invention where Z is (Z2) that is

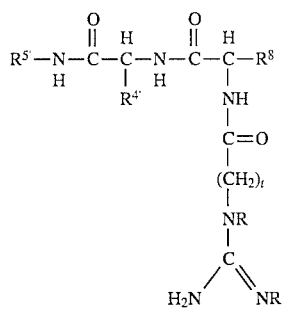

may be prepared according to the following Reaction Sequence IX.

Reaction Sequence IX

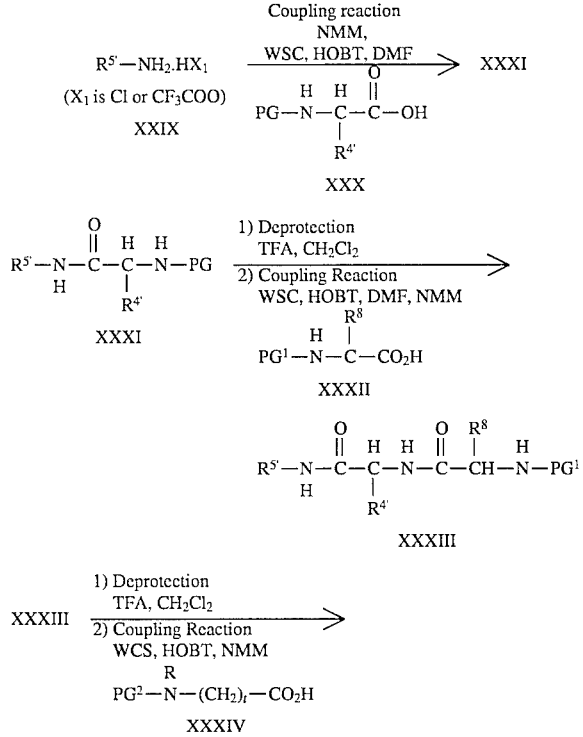

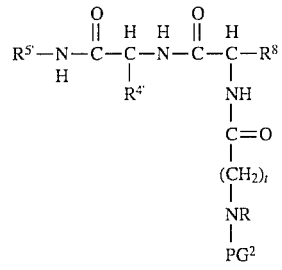

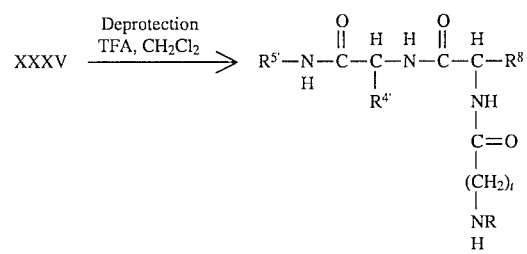

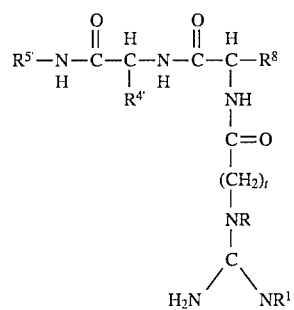

PG, PG$^1$, and PG$^2$ may be the same or different and are protecting groups such as t-butoxycarbonyl or benzyloxycarbonyl.

Referring to the above Reaction Sequence IX, compounds of formula I of the invention where Z is (Z2) may be prepared starting with amine XXIX which is made to undergo a carbodiimide coupling reaction with protected amino acid XXX in the presence of ethyl 3-(3-dimethylamino)propylcarbodiimide hydrochloride (WSC) or dicyclohexylcarbodiimide (DCC), 1-hydroxy-benzotriazole (HOBT) monohydrate, N-methylmorphine (NMM), and an inert organic solvent such as dimethylformamide (DMF) or dichloromethane under an inert atmosphere, such as argon, to form amide XXXI.

Amide XXXI is subjected to a deprotection reaction wherein amide XXXI (if P=butoxycarbonyl) is treated with trifluoroacetic acid (TFA) in the presence of dry inert organic solvent such as dichloromethane, under an inert atmosphere such as argon, at reduced temperature of from about 0° to about 20° C., to form the TFA salt. The TFA salt is added to a mixture of protected amino acid XXXII, HOBT, WSC or DCC, in solvent under an inert atmosphere such as argon at a reduced temperature of from about 0° to about 20° C. NMM is added and the reaction is allowed to go to completion to form dipeptide XXXIII.

Dipeptide XXXIII is then deprotected with TFA to form the TFA salt which is coupled with protected amino acid XXXIV employing WSC or DCC, HOBT and NMM to form protected tripeptide XXXV.

The protected tripeptide XXXV is deprotected to tripeptide XXXVI which is subjected to a modified guanidine forming reaction by, for example, reaction with cyanogen bromide in the presence of sodium acetate and an alcohol solvent such as methanol, and then reaction with amine A or cyanide B in the presence of acid, such as HCl, alcohol such as methanol and weak base such as sodium carbonate, to form compound of the invention IY.

The compounds of formula I of the invention where Z is (Z3), that is

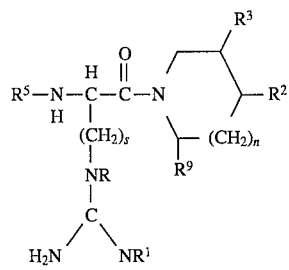

may be prepared according to the following Reaction Sequence X.

Reaction Sequence X

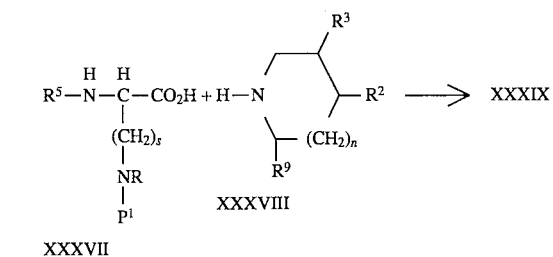

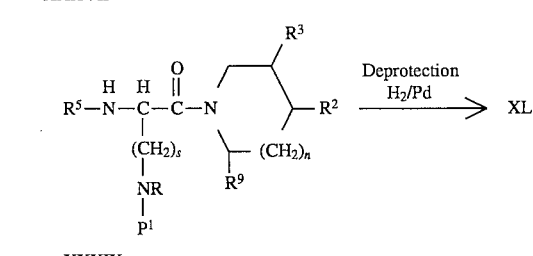

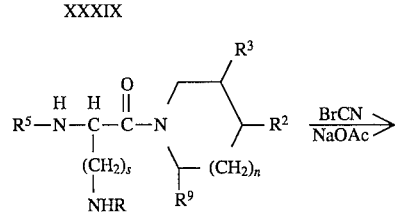

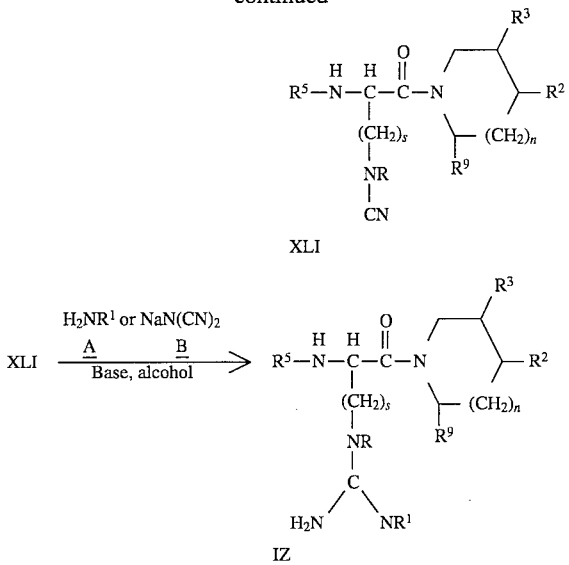

As seen in Reaction Sequence IX, compounds of the invention I wherein Z is (Z3), that is $I^{VII}$ may be prepared by coupling acid XXXVII with compound XXXVIII in the presence of ethyl-3-(3-dimethylamino)propyl carbodiimide hydrochloride and 1-hydroxybenzotriazole hydrate, N-methyl morpholine and an inert organic solvent such as dimethylformamide (DMF) to form amide XXXIX. Amide XXXIX is deprotected by treating XXXIX with $H_2$/Pd to form amide XL which is treated with cyanogen bromide in the presence of sodium acetate to form cyanide XLI. The cyanide XLI is then treated with amine A or cyanide B in the presence of base such as triethylamine, and alcohol solvent such as methanol to form compound IZ of the invention.

The compounds of formula I of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like.

The compounds of the present invention are serine protease inhibitors, and in particular may inhibit thrombin, Factor Xa, and/or trypsin. The compounds of the present invention are useful for the treatment or prophylaxis of those processes which involve the production and/or action of thrombin. This includes a number of thrombotic and prothrombotic states in which the coagulation cascade is activated which include, but are not limited to, deep vein thrombosis (DVT), disseminated intravascular coagulopathy (DIC), Kasabach-Merritt syndrome, pulmonary embolism, myocardial infarction, stroke, thromboembolic complications of surgery (such as hip replacement and endarterectomy) and peripheral arterial occlusion. In addition to its effects on the coagulation process, thrombin has been shown to activate a large number of cells (such as neutrophils, fibroblasts, endothelial cells, smooth muscle cells). Therefore, the compounds of the present invention may also be useful for the treatment or prophylaxis of adult respiratory distress syndrome, septic shock, septicemia, inflammatory responses which include, but are not limited to, edema, acute or chronic atherosclerosis, and reperfusion damage.

The compounds of the invention may also be useful in treating neoplasia/metastasis (in particular those which utilize fibrin) and neurodegenerative diseases such as Alzheimer's disease and Parkinson's disease. In addition, the compounds of the present invention may be useful to prevent restenosis following arterial injury induced by endogenous (rupture of an atherosclerotic plaque) or exogenous (invasive cardiological procedure) events.

The compounds of the present invention may also be used as an anticoagulant in extracorpeal blood circuits, such as those necessary in dialysis and surgery (such as coronary artery bypass surgery).

The compounds of the present invention may also be used in combination with thrombolytic agents, such as tissue plasminogen activator (natural or recombinant), streptokinse, urokinase, prourokinase, anisolated streptokinase plasminogen activator complex (ASPAC), animal salivary gland plasminogen activators, and the like. The compounds of the present invention may act in a synergistic fashion to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also be used in combination with other antithrombotic or anticoagulant drugs such as thromboxane receptor antagonists, prostacyclin mimetics, phosphodiesterase inhibitors, fibrinogen antagonists, and the like.

Compounds of the present invention that inhibit trypsin may also be useful for the treatment of pancreatitis.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc., as called for by accepted pharmaceutical practice.

The following Examples represent preferred embodiments of the present invention. Unless otherwise indicated, all temperatures are expressed in degrees Centigrade.

EXAMPLE 1

N-[[1-[(Hydroxyamino)iminomethyl]-4-piperidinyl]-methyl]-1-[N-[(phenylmethyl)sulfonyl]-D-phenylalanyl]-L-prolinamide, Trifluoroacetate (1:1) Salt

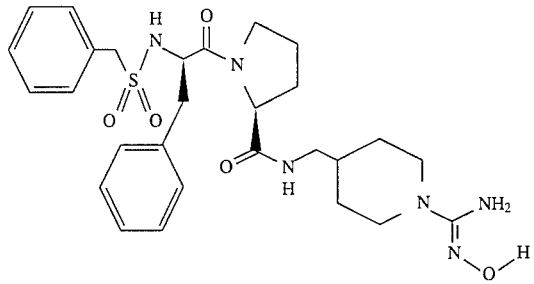

A. N-[(1,1-Dimethylethoxy)carbonyl]-4-methylamino Piperidine

Benzaldehyde (14.6 g, 0.138 mmol), 4-(aminomethyl)-piperdine (14.29 g, 0.125 mmol) and toluene (250 mL) were combined and heated at reflux for 4.5 h with removal of water. The reaction mixture was cooled to −25° C. and di-t-butyl dicarbonate (28.7 g, 0.131) was added. The reaction mixture was allowed to warm to room temperature and stirred an additional 8 h. To this reaction mixture was added aqueous $KHSO_4$ (1.0M, 120 mL) and stirred for 3 h. The organic layer was removed and the remaining aqueous layer was extracted with ether (3×75 mL). The aqueous layer was made basic through the addition of aqueous NaOH (1.0M, 130 mL) and extracted with ether (3×75 mL). The combined organic extracts were dried over $NaSO_4$ filtered, and the solvent removed in vacuo to give title compound, 24.4 g (91%), as a white solid.

B. N-[(Phenylmethoxy)-carbonyl]-D-phenylalanyl-L-proline Methyl Ester

To a solution of N-CBZ-D-phenylalanine (47.3 g, 0.158 mmol) in DMF (300 mL) at 0° C., was added L-proline-methylester.HCl (25.0 g, 0.151 mmol), 1-hydroxybenzotriazole hydrate (20.28 g, 0.166 mmol), ethyl-3-(3-dimethylamino)-propyl carbodiimide.HCl (31.8 g, 0.166 mmol) and 4-methylmorpholine (16.0 g, 0.159 mmol). The reaction mixture was stirred for 8 h while allowing the reaction to warm to room temperature. The reaction mixture was poured in water (1.2 L) and extracted with ethyl acetate (3×300 mL). The combined organic extracts were washed as follows: $KHSO_4$ (0.25M, 2×200 mL), water (1×200 mL), saturated aqueous $NaHCO_3$ (2×200 mL) and saturated NaCl (1×200 mL). The organic layer was dried over $MgSO_4$, filtered and the solvent removed in vacuo to give title compound, 60.9 g (98 %), as an oil.

C. N-[(Phenylmethoxy)-carbonyl]-D-phenyl-alanyl-L-proline

To a solution of Part B compound (57.8 g, 0.141 mol) in MeOH (180 mL) and THF (60 mL) at 0° C. was added aqueous NaOH (1.0N, 183 mL). After 30 min the reaction mixture was warmed to room temperature and stirring continued for an additional 4 h. Aqueous HCl (1.0N, 42 mL) was added and the organic solvents removed in vacuo. The resulting aqueous layer was acidified to pH of 2–3 and extracted with ethyl acetate (2×300 mL). The combined extracts were dried over MgSO₄, filtered and the solvent removed in vacuo to give title compound, 45.53 g (97%), as a white solid.

D. N-[[1-[(1,1-Dimethylethoxy)carbonyl]-4-piperidinyl]methyl]-1-[N-[(phenylmethoxy)-carbony]-D-phenylalanyl]-L-prolinamide To a solution of Part C compound (19.39 g, 48.90 mmol) in DMF (120 mL) at 0° C., was added Part A compound (9.98 g, 46.57 mmol), 1-hydroxybenzotriazole hydrate (6.26 g, 51.23 mmol) and ethyl-3-(3-dimethylamino)propyl carbodiimide HCl (9.82 g, 51.23 mmol). The reaction mixture was stirred for 12 h while allowing the reaction to warm to room temperature. The reaction mixture was poured in water (500 mL) and extracted with ethyl acetate (3×100 mL). The combined organic extracts were washed as follows: KHSO₄ (0.25M, 2×50 mL), water (1×75 mL), saturated aqueous NaHCO₃ (2×75 mL) and saturated NaCl (1×50 mL). The organic layer was dried over MgSO₄, filtered and the solvent removed in vacuo to give title compound, 23.4 g (85%), as an oil.

E. N-[[1-[(1,1-Dimethylethoxy)carbonyl]-4-piperidinyl]methyl]-1-[D-phenylalanyl]-L-prolinamide To a stirred solution of Part D compound (15.00 g, 25.3 mmol) in MeOH (150 mL) was added Pd/C (1.50 g) and the reaction mixture was placed under 1 atmosphere of hydrogen. An additional Pd/C (2.5 g) was added after stirring for 2 h. The reaction was complete after stirring 8 more hours. The reaction mixture was filtered and the solvent removed in vacuo to give title compound, 11.41 g (91%), as a white solid.

F. N-[[1-[(1,1-Dimethylethoxy)carbonyl]-4-piperidinyl]methyl]-1-[N-[(phenylmethyl)-sulfonyl]-D-phenylalanyl]-L-prolinamide To a solution of Part E compound (1.21 g, 2.5 mmol) and triethylamine (1.1 mL, 7.9 mmol) in chloroform (5.7 mL) at 0° C. under argon was added benzylsulfonyl chloride (0.482 g, 2.5 mmol). After 3.25 hr, triethylamine (0.5 mL, 3.6 mmol) and benzylsulfonyl chloride (0.39 g, 2.0 mmol) were added. After 2.75 h, the mixture was diluted with 0.25M aqueous KHSO₄ and EtOAc. After separaton of the two layers, the organic layer was washed with 0.25M aqueous KHSO₄, H₂O, saturated aqueous NaHCO₃, and H₂O, successively; dried over NaSO₄, filtered and concentrated in vacuo to give title compound, 1.37 g (90%).

G. N-[[1-[(1-Dimethylethoxy)carboxyl]-4-(N-cyano)piperidinyl]methyl]-1-[N-[(phenylmethyl)sulfonyl] -D-phenylalanyl]-L-prolinamide To a solution of Part F compound (1.4 g, 2.2 mmol) in dichoromethane (9.0 mL) under nitrogen at 0° C. was added 4N HCl-dioxane (14 mL, 25 mmol)). After 5 min., the 0° C. bath was removed. The reaction was stirred for 1.5 h and concentrated in vacuo to give crude N-(4-piperidinyl)methyl-1-[N-[(phenylmethyl)sulfonyl] -D-phenylalanyl]-L-prolinamide, hydrochloride salt. To a solution of crude HCl salt (2.24 mmol), triethylamine (1.3 mL, 9.3 mmol) and sodium acetate (0.74 g, 9.6 mmol) in methanol (10 mL) was added cyanogen bromide (0.71 g, 6.7 mmol). After 21.5 h, the reaction mixture was concentrated in vacuo. The material was dissolved in EtOAc and H₂O. After separation, the organic layer was dried over MgSO₄, filtered and concentrated in vacuo to give crude title compound.

H. N-[[1-[(Hydroxyamino)iminomethyl]-4-piperidinyl]methyl]-1-[N-[(phenylmethyl)sulfonyl]-D-phenylalanyl]-L-prolinamide, Trifluoroacetate (1:1) Salt To crude Part G compound was added a solution of hydroxylamine in methanol [prepared by stirring hydroxylamine.HCl (1.9 g, 27.0 mmol) and Na₂CO₃ (1.4 g, 13.5 mmol) in methanol (36 mL) for 15 min. and filtering the precipitate]. After 7.5 h, the precipitate was filtered, and the filtrate was concentrated in vacuo and purified by preparative HPLC to give title compound, 0.20 g (11%) as a white solid:

[α]$_D$=−44.5° (c=0.56, MeOH)

Anal. Calc'd for C₂₈H₃₈N₆O₅S.1.2 TFA.1.05 H₂O: C, 50.26; H, 5.73; N, 11.57; S, 4.41; F, 9.41 Found: C, 50.26; H, 5.81; N, 11.50; S, 4.10; F, 9.42

EXAMPLE 2

N-[[1-[(Cyanoamino)iminomethyl]-4-piperidinyl]-methyl]-1-[N-[(phenylmethyl)sulfonyl]-D-phenylalanyl]-L-prolinamide

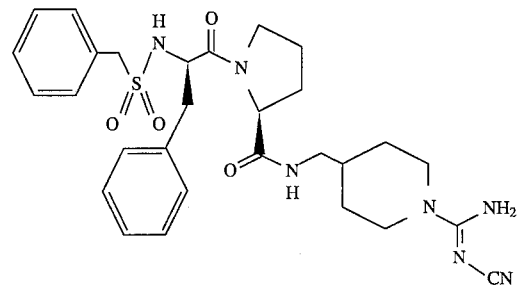

To a stirred mixture of Example 1 Part G compound (500 mg, 0.89 mmol) in 10 mL of n-BuOH under argon was added sodium dicyanamide (197 mg, 2.22 mmol). This mixture was heated to reflux under argon for 18 h and cooled to room temperature. The mixture was concentrated in vacuo and diluted with 240 mL of EtOAc. The solution was washed with 0.25M KHSO₄ solution (2×60 mL), saturated NaHCO₃ solution (1×60 mL) and brine (1×60 mL), the organic layer dried (MgSO₄), filtered and concentrated in vacuo, and chromatographed on silica gel to give 260 mg (50%) of title compound.

[α]$_D$=−62.1° (c=0.94, CHCl₃)

Anal. Calc'd for C₂₉H₃₇N₇O₄S.0.26H₂O: C, 59.59; H, 6.47; N, 16.78; S, 5.49 Found: C, 59.34; H, 6.52; N, 17.03; S, 5.33 mp 125°–130° C.

EXAMPLE 3

N-[[1-[(Hydroxyamino)iminomethyl]-
4-piperidinyl]-methyl]-1-[N-[methylsulfonyl]-
D-phenylalanyl]-L-prolinamide

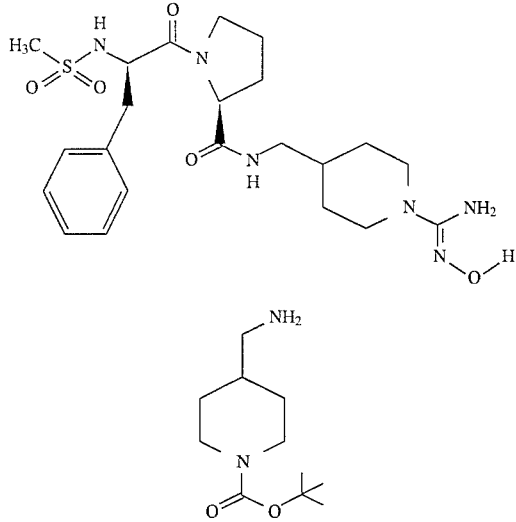

A.

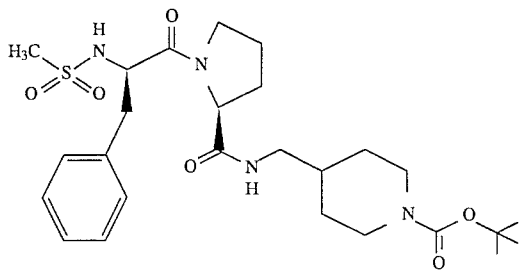

Following the procedure published in Synthetic Communication, 22(16), p 2357–2360, 1992, the title compound was obtained.

B.

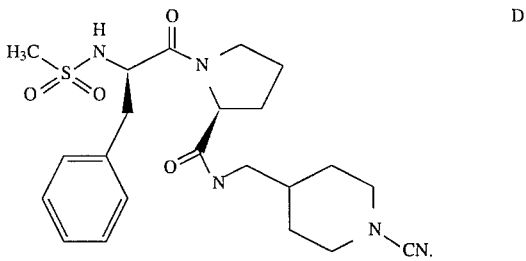

To a stirred solution of methylsulfonamido-D-phenylalanylproline (3.18 g, 9.35 mmol), Part A amine (2.00 g, 9.35 mmol) and 1-hydroxybenzotriazole monohydrate (1.58 g, 9.35 mmol) in 60 mL of DMF was added in order N-methylmorpholine (3.29 mL, 29.9 mmol) and ethyl-3-(3-dimethylamino)propyl carbodiimide hydrochloride (1.79 g, 9.35 mmol). The reaction solution was stirred at room temperature for 20 h and concentrated under pump vacuum at 45° C. The oily residue was dissolved in 300 mL of EtOAc and washed with 1N HCl solution (2×150 mL), saturated NaHCO₃ solution (2×150 mL) and brine (1×150 mL). The organic layer was dried (MgSO₄), filtered, concentrated in vacuo and chromatographed on Merck silica gel to give 4.21 g (84%) of title carbamate.

C.
N-[(4-Piperidinyl)methyl]-1-[N-[(methyl)sulfonyl]
-D-phenylalanyl]-L-prolinamide, Hydrochloride Salt

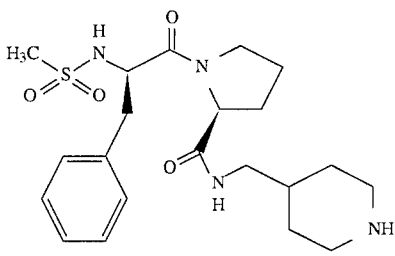

To a stirred solution of Part B carbamate (1.25 g, 2.33 mmol) in 10 mL of dichloro-methane was added 0° C. 4N HCl in dioxane (15.0 mL, 60.0 mmol). The reaction solution was stirred at room temperature for 1 h and concentrated in vacuo. The oily residue was dissolved in 40 mL of methanol and then concentrated in vacuo to give 1.10 g (quantitative) of title amine hydrochloride.

D

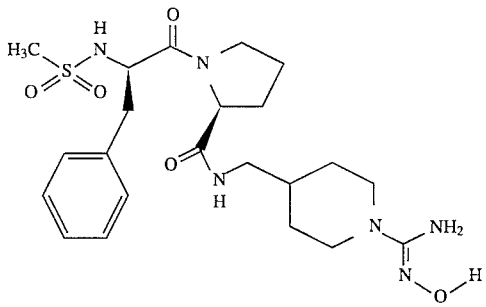

To a stirred solution of Example 3 Part C amine.HCl (1.36 g, 2.88 mmol) and anhydrous NaOAc (1.18 g, 14.4 mmol) in 10 mL of methanol was added cyanogen bromide (0.61 g, 5.76 mmol). This heterogeneous mixture was stirred at room temperature for 3.5 h and concentrated in vacuo. Purification was effected by flash chromatography on silica gel to give 1.30 g (98%) of title aminonitrile. 6% CH₃OH/CH₂Cl₂, $R_f$=0.55, I₂.

E. N-[[1-[(Hydroxyamino)iminomethyl]-4
-piperidinyl]-methyl]-1-[N-(methylsulfonyl)-
D-phenylalanyl]-L-prolineamide To a stirred solution of hydroxyamine hydrochloride (2.01 g, 28.9 mmol) in 38 mL of methanol was added solid sodium carbonate (1.52 g, 14.3 mmol). This suspension was stirred at room temperature for 15 min and the insoluble material filtered off. The filtrate was then combined with Part D compound, the reaction stirred at room temperature for 3 h, concentrated in vacuo and purified by preparative HPLC to give 580 mg (33%) of the title compound.

[α]$_D$=–57.5° (c=0.52, MeOH)

Anal. Calc'd for $C_{22}H_{34}N_6O_5S.2.30C_2F_3O_2H$: C, 42.21; H, 4.83; N, 11.10; S, 4.24; F, 17.32 Found: C, 42.21; H, 4.98; N, 10.91; S, 4.36; F, 17.13

EXAMPLE 4

N-[[1-[(Cyanoamino)iminomethyl]-4-piperidinyl]-
methyl]-1-[N-[(methyl)sulfonyl]-
D-phenylalanyl]-L-prolinamide

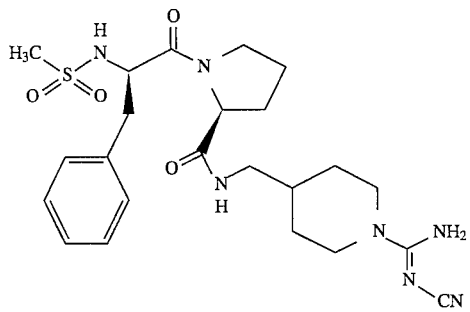

To a stirred solution of Example 3 Part D compound (220 mg, 0.40 mmol) in 3.0 mL of n-BuOH was added sodium dicyanamide (99.0 mg, 1.00 mmol). The reaction mixture was heated to reflux for 14 h and concentrated in vacuo. This was purified by preparative HPLC to give 124 mg (57%) of title compound.

Anal. Calc'd for $C_{23}H_{33}N_7O_4S.0.80H_2O.0.25C_2F_3O_2H$: C, 51.65; H, 6.43; N, 17.94; S, 5.87; F, 2.61 Found: C, 51.68; H, 6.45; N, 18.29; S, 5.58; F, 2.81

EXAMPLE 5

N-[[1-[(Methoxyamino)iminomethyl]-
4-piperidinyl]-methyl]-1-[N-[(methyl)sulfonyl]-
D-phenylalanyl]-L-prolinamide

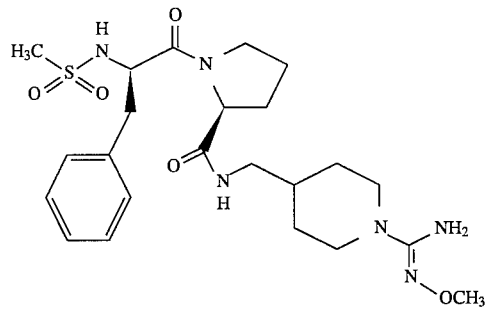

To a stirred solution of Example 3 Part D aminonitrile (0.34 g, 0.74 mmol) in 3.0 mL of 1-methyl-2-pyrrolidinone was added methoxyamine.HCl (0.18 g, 216 mmol). This reaction solution was immersed into a 85° C. oil bath. The bath temperature was slowly raised up no 130° C. in 80 min. The reaction solution was stirred at 130° C. for 2 h and cooled to room temperature. The solution was diluted with 30 mL of ether and the solution was decanted. The remaining oily residue was purified by preparative HPLC to give 250 mg (51%) of title compound.

Anal. Calc'd for $C_{23}H_{36}N_6O_5S.0.80H_2O.1.25C_2F_3O_2H$: C, 46.02; H, 5.88; N, 12.63; S, 4.82; F, 10.70 Found: C, 46.09; H, 5.73; N, 12.49; S, 4.95; F, 10.69

EXAMPLE 6

1S[2R*(3R*)]]-N-[2-[2[[[[1-((Hydroxyamino)
iminomethyl))-3
-piperidinyl]carbonyl]amino]methyl]-1-pyrrolidinyl]
-1-(hydroxymethyl)-2-oxoethyl]-2-naphthalene
Sulfonamide, Trifluoroacetate Salt

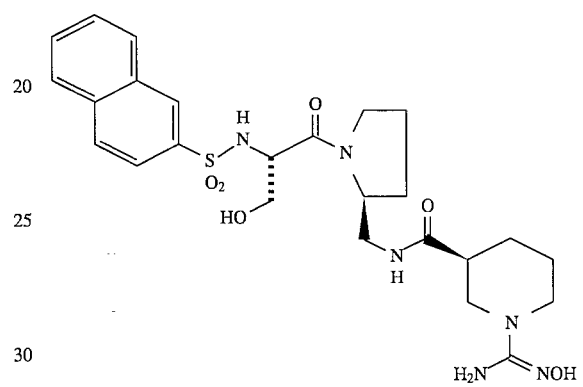

A

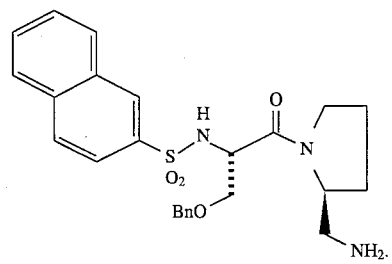

A(1)

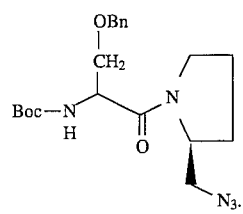

2-Azido-N—BOC pyrrolidine (2.13 g, 9.4 mmol) was dissolved in dichloromethane (5 mL) and trifluoroacetic acid (7 mL) and stirred at RT 3 hours. The TFA and dichloromethane were removed by distillation under reduced pressure and by coevaporation with toluene to give the amine as a TFA salt. This and N-BOC-O-benzyl-L-serine (2.95g, 10 mmol) were dissolved in DMF (50 mL). HOBT (1.35 g, 10 mmol), WSC (1.91 g, 10 mmol) and NMM (3.3 mL, 30 mmol) were added. The reaction was stirred for 8 h at room temperature, diluted with ethyl acetate (50 mL) and saturated KHSO$_4$ solution (30 mL). The layers were separated and the aqueous layer was reextracted with saturated sodium bicarbonate solution (30 mL) and 10% lithium chloride solution (30 mL). The ethyl acetate layer was dried over magnesium sulfate and concentrated in vacuo to provide title A(1) compound (3.87 g, 100%) as an oil which was used without further purification.

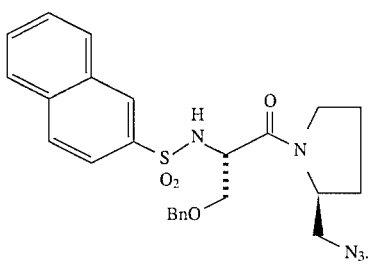

A(2)

Part A(1) BOC-azide (3.85 mg, 9.55 mmol) was dissolved in TFA (20 mL) and stirred at RT 1.5 hours. The TFA was removed by distillation under reduced pressure and by coevaporation with toluene. The residue was dissolved in dichloromethane (100 mL), cooled in an ice bath, and triethylamine (4.0 mL, 28.7 mmol) and 2-naphthyl sulfonyl chloride (2.00 g, 10.5 mmol) were added. The cooling bath was removed and the solution was stirred for 2 h. This solution was washed with KHSO$_4$ solution (25mL×2) and NaHCO$_3$ solution(25 mL×2), dried over magnesium sulfate and evaporated to provide crude A(2) which was chromatographed on silica gel to provide A(2) sulfonamide (2.60 g, 55%).

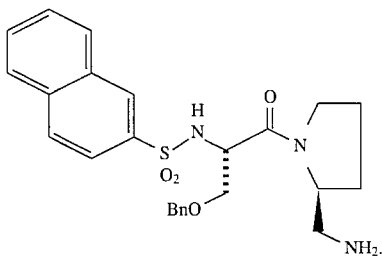

A(3)

The Part A(2) azide (2.5 g, 5 mmol) was dissolved in absolute ethanol (100 mL) and treated with 10% palladium on carbon (300 mg) and hydrogen gas at room temperature overnight. The catalyst was then removed by filtration through Celite, the pad washed with ethanol, and the solvent removed in vacuo to give title A amine as a foam (2.24 g, 96%).

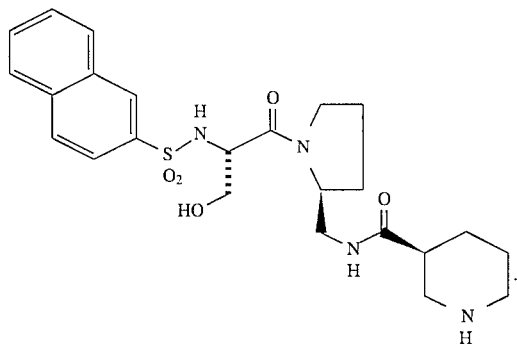

B

B(1). Ethyl Nipecotate, D-tartrate Salt

Ref: Johnston, G. A. R. et al, J Neurochemistry, 1976, Vol 26, pp.1029–1032. Ethyl nipecotate (50 g, 318 mmol) and D-tartaric acid (47.74 g, 318 mmol)were dissolved in hot abs. ethanol (250 mL). A very small amount of insoluble material was removed by filtration through a pad of Celite. The filtrate gave crystalline material on cooling. This was harvested and recrystallized eight times from absolute ethanol to give title compound as a white solid (27 g). m.p. 155°–156° C., [α]$_{365}$=–200.7° (c=2.0, 0.2% aqueous ammonium molybdate).

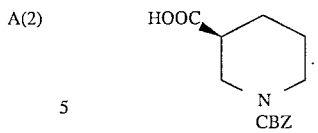

B(2)

The Part B(1) tartrate salt (1.0 g) was dissolved in water (5 mL) and a solution of potassium carbonate was added to bring the pH to 9. The solution was cooled in an ice water bath and ether (5 mL) was added. Benzyl chloroformate (0.5 mL) was added dropwise to the well-stirred solution. During the addition, the pH was maintained between 8 and 9 by addition of potassium carbonate solution. After addition was complete, the mixture was stirred cold for an additional 1.5 hours, maintaining the pH thoughout this period. The layers were separated and the aqueous was reextracted with ether. The combined ether layers were dried over magnesium sulfate and concentrated in vacuo. The ethyl ester obtained was purified on silica gel, the purified material (930 mg) was dissolved in methanol (8 mL) and treated with 1N NaOH solution (4 mL). After stirring at room temperature two hours, the methanol was removed in vacuo. The aqueous solution was acidified with 1N HCl and the acid was extracted into ethyl acetate (2×10 mL), the combined extracts dried over magnesium sulfate and concentrated in vacuo to give title compound as a crystalline solid. (773 mg). [α]$_D$=+49.9° (c=1.4, MeOH). The optical purity of this material was determined by coupling some of this material with (S)-(-)-a-methyl-benzylamine. The material obtained was submitted to analytical HPLC for determination of purity and was found to be 97.6%, (e.e.=95.2%).

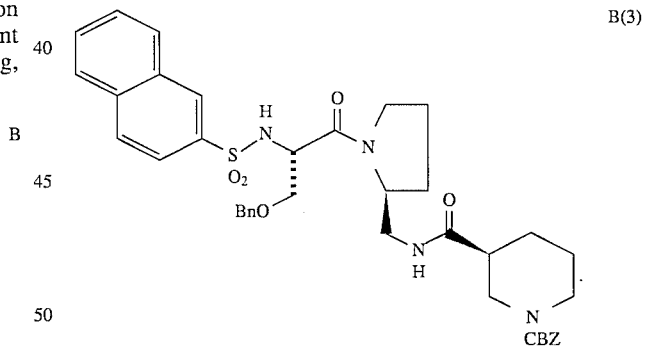

B(3)

Part A amine (820 mg, 1.75 mmol) and Part B(2) acid (526 mg, 2.0 mmol) were dissolved in DMF (20 mL) at RT. HOBT (270 mg, 2 mmol), N-methyl morpholine (1.5 mL) and WSC (400 mg, 2 mmol) were added. The reaction was stirred 24 hours at room temperature. The mixture was then diluted with ethyl acetate (75 mL) and KHSO$_4$ solution (30 mL) and the layers were separated. The organic layer was washed with saturated NaHCO$_3$ solution (20 mL) and 10% lithium chloride solution (2×20 mL), dried over magnesium sulfate and concentrated in vacuo. The crude oil was chromatographed on silica gel, eluting with 50% EtOAc in hexane followed by 70% EtOAc in hexane and finally with EtOAc to provide title compound as a foam (830 mg, 67%).

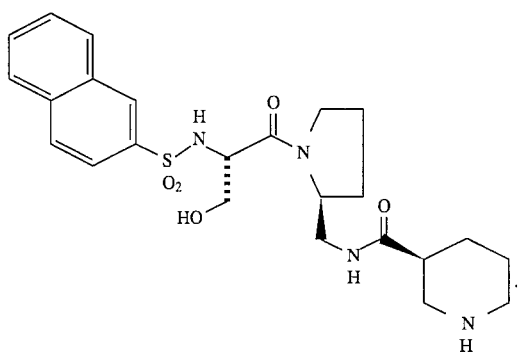
B(4)

Part B(3) compound (820 mg, 1.15 mmol) was dissolved in ethanol (100 mL) to which acetyl chloride (2.5 mL) had been added and the mixture was treated with 10% palladium on carbon (250 mg) and hydrogenated at 55 psi for 44 h. The catalyst was removed by filtration and the pad was washed with EtOH. The filtrate was concentrated in vacuo to obtain crude title B compound.

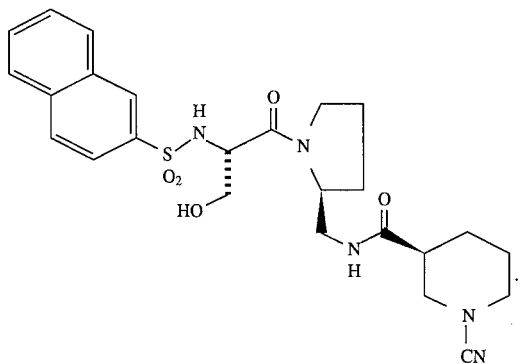
C

The crude Part B hydrochloride salt (509 mg, 0.97 mmol) was dissolved in methanol (4 mL) and sodium acetate (463 mg) was added. While stirring, a solution of cyanogen bromide (117 mg, 1.1 mmol) in methanol (15 mL) was added dropwise over a period of three hours. Additional sodium acetate (600 mg) was added and stirring was continued for four hours. The solvent was removed in vacuo and the residue was partitioned between water and dichloromethane. The layers were separated and the dichloromethane solution was dried over magnesium sulfate, filtered and freed of solvent in vacuo to give title compound (464 mg) which was used without purification.

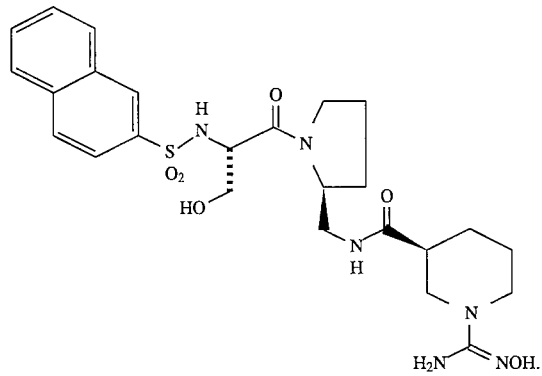
D

Hydroxylamine hydrochloride (647 mg, 9.3 mmol) in methanol (10 mL) was treated with sodium carbonate (492 mg, 4.65 mmol). The mixture was stirred 15 minutes and filtered. The filtrate was added to the crude Part A cyano compound (0.93 mmol) and stirred at room temperature for three hours. The solvent was removed in vacuo. The crude material was purified by preparative HPLC to provide title compound as a white solid (315 mg, 49%).

[α]$_D$=15.5° (c=0.5, MeOH)

Analysis calcd for 1.2 TFA+0.7 H$_2$O: C, 47.28; H, 5.30; N, 12.07; F, 9.83; S, 4.61. Found: C, 47.16; H, 5.25; N, 12.44; F, 9.79; S, 4.48.

EXAMPLE 7

[1S[2R*]]-N-[2-[2[[[[1-((Hydroxyamino) iminomethyl))-4 -phenyl]carbonyl]amino]methyl]-1-pyrrolidinyl]- 1-(hydroxymethyl)-2 -oxoethyl]-2-naphthalene Sulfonamide, Trifluoroacetate Salt

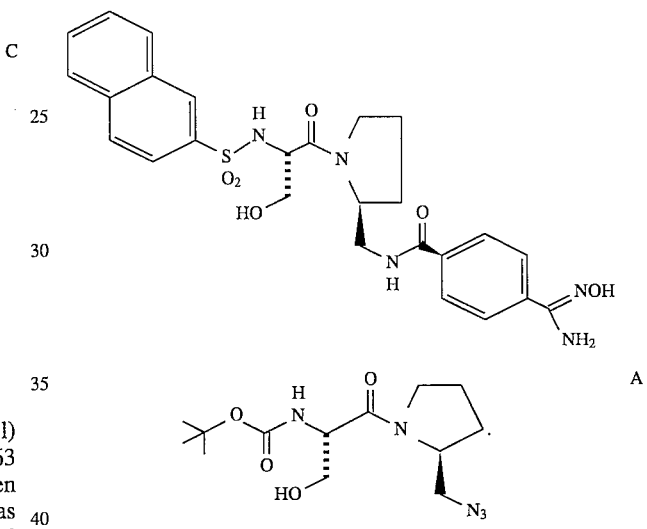
A

To a stirred solution of 1-BOC-2-(methylazide)pyrrolidine (12.54 g, 55.5 mmol) in 10 mL of dry dichloromethane at 0° C. was added a solution of 4N HCl in dioxane (25.0 mL, 100 mmol). The solution was stirred at room temperature for 2.5 h and concentrated in vacuo to give a crude amine as an oil. To a stirred solution of this amine, N-Boc-L-serine (11.4 g, 55.5 mmol) and 1-hydroxybenzotriazole monohydrate (9.37 g, 55.5 mmol) in 240 mL of DMF was added in order N-methylmorpholine (18.3 mL, 167 mmol) and ethyl 3-(3-dimethyl amino)propyl carbodiimide hydrochloride (10.6 g, 55.5 mmol). The reaction solution was stirred at room temperature for 19 h and concentrated under pump vacuum at 45° C. The residue was dissolved in 1 L of EtOAc and washed with 5%KHSO$_4$ solution (3×0.5 L), saturated NaHCO$_3$ solution (2×0.5 L) and brine (1×0.5 L). The EtOAc layer was dried (MgSO$_4$), filtered and concentrated in vacuo to give 14.4 g (83%) of title A amide.

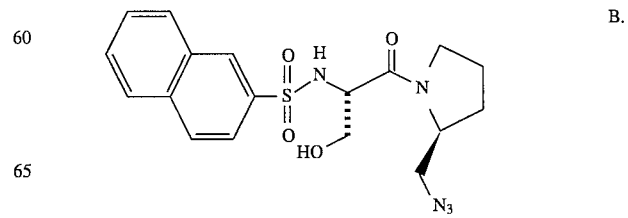
B.

To a stirred solution of Part A amide (14.3 g, 45.9 mmol) in 20 mL of dry dichloromethane at 0° C. was added a solution of 4N HCl in dioxane (40.0 mL, 160 mmol). The solution was stirred at room temperature for 2 h and concentrated in vacuo to give a crude amine as an oil. To a stirred solution of this amine and triethylamine (15.4 mL, 110 mmol) in 100 mL of dry dichloromethane at 0° C. was added dropwise a solution of 2-naphthalenesulfonyl chloride (10.9 g, 48.2 mmol) in 60 mL of dry dichloromethane over 40 min. The reaction solution was stirred at 0° C. for 1 h and at room temperature for 2 h. The solution was diluted with 1 L of dichloromethane and washed with 1N HCl solution (3×0.5 L), saturated NaHCO₃ solution (2×0.5 L) and brine (1×0.5 L). The dichloromethane layer was dried (MgSO₄), filtered, concentrated in vacuo and triturated in EtOAc-hexane to give 11.5 g of Part B azide. The triturant was concentrated in vacuo and chromatographed on silica gel to give 1.4 g of title azide.

C.

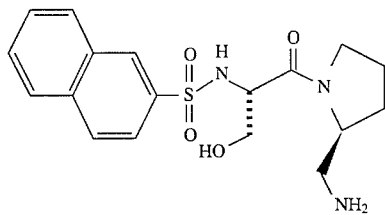

To a stirred solution of Part B azide (11.2 g, 27.8 mmol) in 300 mL of EtOH and 600 mL of methanol was added 10%Pd/C (2.24 g). The atmosphere was replaced with hydrogen and the reaction mixture was stirred at room temperature for 17 h. The catalyst was filtered off, and rinsed with methanol, and the filtrate concentrated in vacuo to give 9.9 g (94%) of crude Part C amine.

D.

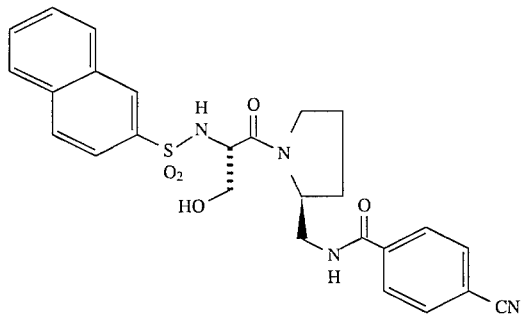

Part C amine (1.93 g, 5.15 mmol), 4-cyanobenzoic acid (757 mg, 5.15 mmol) and 1-hydroxybenzotriazole (869 mg, 6.44 mmol) were dissolved in DMF (30 mL) at RT. N-Methylmorpholine (1.1 mL, 10 mmol) was added dropwise followed by WSC (1.03 g, 5.15 mmol). The reaction was stirred 20 hours at room temperature, the mixture diluted with ethyl acetate (75 mL) and KHSO₄ solution (60 mL), the layers separated and the aqueous layer was reextracted with ethyl acetate (75 mL). The combined organic layer was washed with sat'd. NaHCO₃ solution (50 mL) and 10% lithium chloride solution (2×25 mL), dried over magnesium sulfate and concentrated in vacuo. The crude product was chromatographed on silica gel, to provide Part D compound as a foam (2.01 g, 78%).

E.

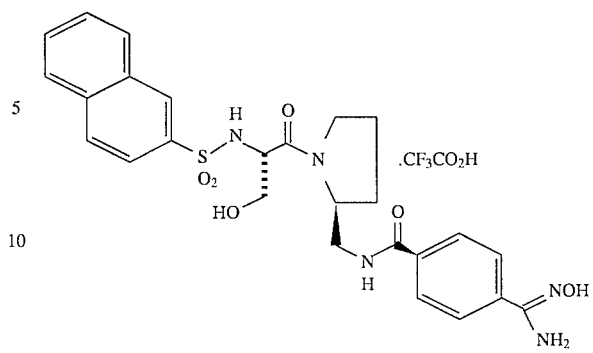

Hydroxylamine hydrochloride (700 mg, 10 mmol) in methanol (10 mL) was treated with sodium carbonate (540 mg, 5 mmol). The mixture was stirred 15 minutes and filtered. The filtrate was added to the Part D cyano compound (1.0 mmol) and stirred at room temperature for eighteen hours. The solvent was removed in vacuo. The crude material was purified by preparative HPLC to provide title compound as a white solid (398 mg, 57%).

$[\alpha]_D = -36.9°$ (C=0.7, MeOH)

Analysis calcd for 1.15 TFA+1.3 H₂O: C, 48.97; H, 4.76; N, 10.09; F, 9.44; S, 4.62. Found: C, 49.24; H, 4.79; N, 9.70; F, 9.20; S, 4.85.

EXAMPLE 8

(S)-N<2-[N-[4-[(Hydroxyaminoiminomethyl)amino]-1-oxobutyl]-4-nitro-L-phenylalanyl]-N-(1-phenylethyl)-L-allo-threoninamide

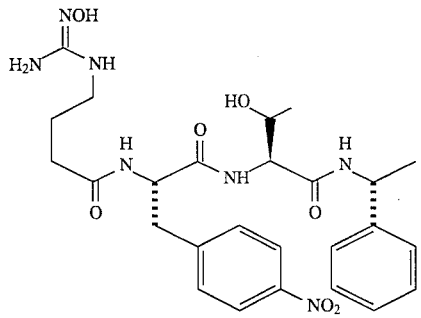

A. (R)-N²-[(1,1-Dimethylethoxy)carbonyl]-N-(1-methyl-2-phenylethyl)-L-allothreoninamide To a solution of N-Boc-L-allothreonine (0.325 g, 1.48 mmol, 1.00 eq.) and 1-hydroxybenzotriazole hydrate (0.221 g, 1.64 mmol, 1.11 eq.) in dimethylformamide (5 mL) at 0° C. was added 1-(3-dimethylaminopropyl)-2-ethylcarbodiimide hydrochloride (WSC) (0.312 g, 1.63 mmol, 1.10 eq.). After 0.5 hr, a solution of (R) α-methylbenzylamine (0.20 mL, 1.55 mmol, 1.05 eq.) in dimethylformamide (3 mL) was added, followed by 4-methylmorpholine (0.16 mL, 1.46 mmol, 0.98 eq.). After 17 hr, the reaction mixture was poured into a brine/water solution (1:1) and extracted twice with ethyl acetate. The organic layers were combined and washed with aqueous 0.25M potassium hydrogen sulfate, water, aqueous saturated sodium bicarbonate, water, dried over sodium sulfate, and the organic layer concentrated in vacuo to give title compound (0.448 g, 93.9%):

B. (R)-N²-[N-[(1,1-Dimethylethoxy)carbonyl]-4-nitro-L-phenylalanyl]-N-(1-methyl-2-phenylethyl)-L-allothreoninamide To a solution of Part A compound (0.418 g, 1.29 mmol, 1.00 eq.) in dichloromethane (2.2 mL) under argon at 0° C. was added trifluoroacetic acid (1.5 mL, 19.5 mmol, 15.1 eq.). After 4.0 hr, trifluoroacetic acid (5 mL, 64.8 mmol, 5.44 eq.) was added. After 5 hr, the reaction mixture was concentrated in vacuo to give the crude TFA salt of Part A compound. To a solution of Boc-4-nitro-L-phenylalanine (0.441 g, 1.42 mmol, 1.10 eq.) and 1-hydroxybenzo-triazole hydrate (0.193 g, 1.43 mmol, 1.10 eq.) in dimethylformamide (5.0 mL) at 0° C. was added 1-(3-dimethylaminopropyl)-2-ethylcarbodiimide hydrochloride (0.273 g, 1.43 mmol, 1.10 eq.). After 0.5 hr, a solution of crude TFA salt of Part A compound (1.29 mmol, 1.00 eq.) in dimethylformamide (3.0 mL) was added, which was then followed by 4-methylmorpholine (0.5 mL, 4.55 mmol, 3.52 eq.). After 21 hr, the reaction mixture was poured into a brine/water solution (1:1) and extracted with ethyl acetate twice. The organic layers were combined and washed with aqueous 0.25M potassium hydrogen sulfate, water, aqueous saturated sodium bicarbonate and water, successively. The organic layer was concentrated in vacuo to give title compound (0.651 g, 98.0%):

C. (R)-N²-[N-[[(1,1-Dimethylethoxy)-carbonyl]amino]-1-oxobutyl]-4-nitro-L-phenylalanyl]-N-(1-methyl-2-phenylethyl)-L-allothreoninamide To a solution of Part B compound (0.6157 g, 1.20 mmol, 1.00 eq.) in dichloromethane (2.0 mL) under argon at 0° C. was added trifluoroacetic acid (1.4 mL, 18.2 mmol, 15.1 eq.). After 5.5 hr, the reaction mixture was concentrated in vacuo to give the crude TFA salt of Part B compound. To a solution of BocNH-(CH₂)₃CO₂H (0.268 g, 1.32 mmol, 1.10 eq.) and 1-hydroxybenzotriazole hydrate (0.179 g, 1.32 mmol, 1.10 eq.) in dimethylformamide (4.4 mL) at 0° C. was added 1-(3-dimethylaminopropyl)-2-ethylcarbodiimide hydrochloride (0.253 g, 1.32 mmol, 1.10 eq.). After 0.5 hr, a solution of crude TFA salt of Part B compound (1.20 mmol, 1.00 eq.) in dimethylformamide (2.4 mL) was added, which was then followed by N-methylmorpholine (0.30 mL, 2.73 mmol, 2.27 eq.). After 22 hr, the reaction mixture was poured into a brine/water solution (1:1) and extracted with ethyl acetate twice. The organic layers were combined and washed with aqueous 0.25M potassium hydrogen sulfate, water, aqueous saturated sodium bicarbonate and water, successively. The organic layer was concentrated in vacuo and the crude solid was washed with diethyl ether to give title compound (0.710 g, 98.7%).

D. (S)-N<2-[N-[4-[(Hydroxyaminoiminomethyl)-amino]-1-oxobutyl]-4-nitro-L-phenylalanyl]-N-(1-phenylethyl)-L-allo-threoninamide To a solution of Part C compound (0.202 g, 0.337 mmol, 1.00 eq.) in dichloromethane (1.8 mL) at 0° C. under argon was added trifluoroacetic acid (1.2 mL). After 4.0 hr, the reaction mixture was concentrated in vacuo to give crude TFA salt of Part C compound. To a solution of crude TFA salt of Part C compound (0.337 mmol, 1.0 eq.) in MeOH (1.5 mL), was added NaOAc (0.138 g, 1.69 mmol). The reaction was stirred for 7 h. To this crude reaction mixture were added NH₂OH.HCl (351 mg, 5.06 mmol) and Na₂CO₃ (268 mg, 2.53 mmol). The reaction mixture was concentrated in vacuo and purified by preparative HPLC to yield title compound (0.045 g, 22%) as a white solid:

Anal. calcd. for C₂₆H₃₅N₇O₇.1.10 TFA.1.50 H₂O: C, 47.46; H, 5.58; N, 13.74; F, 8.78. Found: C, 47.70; H, 5.26; N, 13.37; F, 8.46.

EXAMPLE 9

2R-[1(2S*),2α,4β]]-1-[5-[Amino(hydroxyimino)methyl]-amino]-2-[[(1,2,3,4-tetrahydro-3-methyl-8-quinolylyl)sulfonyl]amino]-1-oxopentyl]-4-methyl-2-piperidinecarboxylic Acid, Ethyl Ester

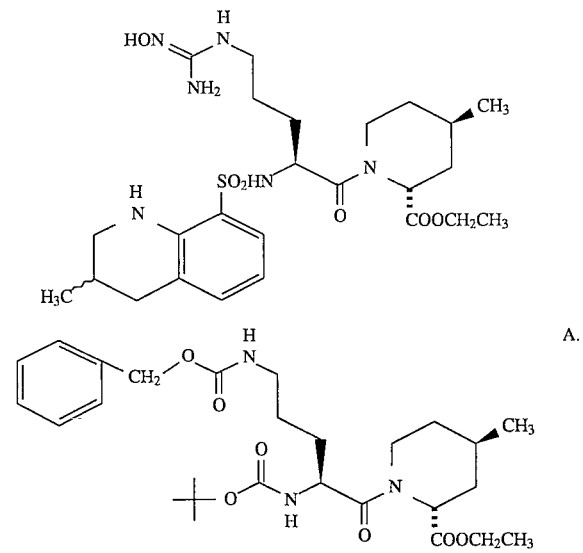

Ethyl-3-(3-dimethylamino)propyl carbodiimide hydrochloride (1.23 g, 6.42 mmol) was added to a solution of α-Boc-γ-CBZ-L-ornithine (2.35 g, 6.42 mmol) and 1-hydroxybenzotriazole (0.98 g, 6.42 mmol) in 26 mL of DMF. After 30 minutes, 2(R)-ethoxycarbonyl-4(R)-methylpiperidine

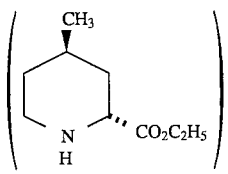

(1.00 g, 5.84 mmol) and 4-methyl-morpholine (0.64 mL, 5.8 mmol) were added, and the reaction was continued for 45 minutes. The reaction was quenched by the addition of 260 mL of 0.25M KHSO₄ solution. The crude product was extracted with EtOAc (2 X 100 mL), the combined EtOAc layers were washed with 0.25M KHSO₄ solution (3 X 50 mL), saturated KHCO₃ solution (3 X 50 mL), brine, dried (Na₂SO₄), and evaporated to yield 3.31 g of a colorless taffy. Flash chromatography on silica gel provided the title compound (2.60 g, 86%) as a colorless gum.

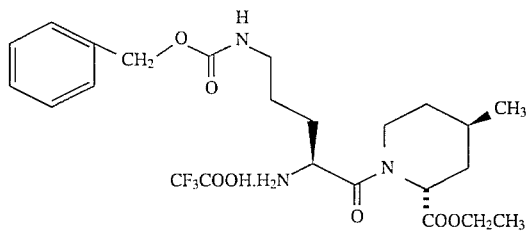
B.

Trifluoroacetic acid (33.0 mL) was added to Part A compound (2.49 g, 4.79 mmol) at 0° C. The solution was stirred for 1 hour at room temperature. Trifluoroacetic acid was removed under vacuum with toluene. The residue was co-evaporated with ether and hexane to yield title compound (2.94 g, ca. 100%) as a gum.

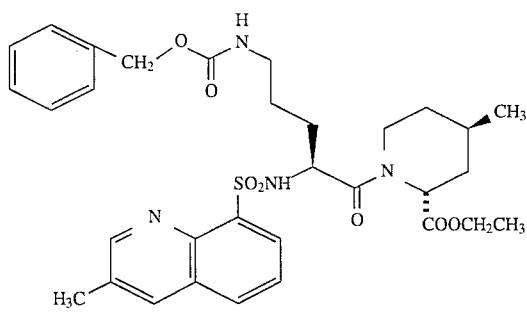
C.

Triethylamine (0.73 mL, 5.3 mmol) followed by 3-methyl-8-chlorosulfonyl quinoline (1.27 g, 5.27 mmol) was added to a solution of Part B compound (2.56 g, 4.79 mmol) in 36.0 mL of $CH_2Cl_2$. After 3 hours, $CH_2Cl_2$ was removed in vacuo, the residue partitioned between EtOAc (30 mL) and 0.25M $KHSO_4$ solution (20 mL), the EtOAc layer was washed with 0.25M $KHSO_4$ solution (3 X 20 mL), saturated aqueous $KHCO_3$ solution (3 X 20 mL), brine, dried ($Na_2SO_4$), and evaporated under reduced pressure to yield 3.18 g of a gum. Flash chromatography on silica gel provided Part C title compound (2.23 g, 75%) as a glass.

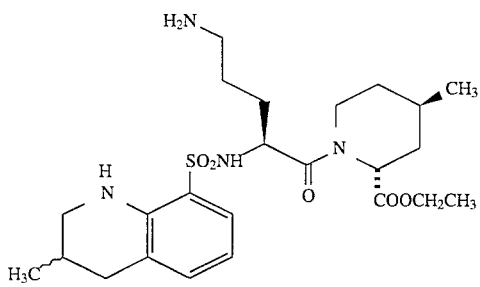
D.

A solution of Part C compound (2.22 g, 3.55 mmol) in 33.0 mL of absolute EtOH with 2.22 g of palladium black was hydrogenated at 1 atmosphere for 3 days. The catalyst was removed by filtration, the filtrate concentrated and co-evaporated with ether and hexane to yield title compound (1.61 g, 92%) as a glass.

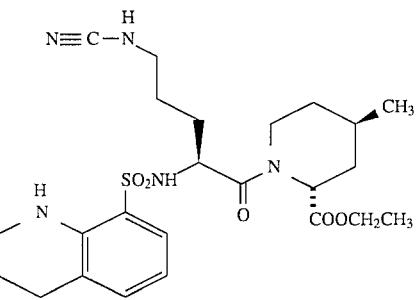
E.

Cyanogen bromide (0.34 g, 3.2 mmol) was added to a solution of Part D compound (1.33 g, 2.69 mmol) and $NH_4OAc$ (0.46 g, 5.96 mmol) in 10.0 mL of $CH_3OH$. After 1 hour, an additional portion of cyanogen bromide was introduced (0.11 g, 1.07 mmol) and the reaction was continued for 24 hours. Methanol was removed under vacuum, and the Part E crude product was used for the next step without purification.

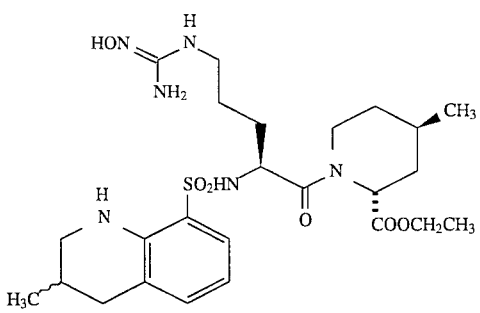
F.

A suspension of hydroxylamine hydrochloride (1.87 g, 26.9 mmol) and sodium carbonate (1.42 g, 13.5 mmol) in 34.0 mL of $CH_3OH$ was stirred for 15 minutes. Insoluble material was removed by filtration and the filtrate was added directly to Part E compound. After 2 hours, the solvent was removed under reduced pressure, and the crude product purified by preparative HPLC to yield title compound (748 mg, 40%) as a colorless solid.

Anal., calcd for $C_{25}H_{40}N_6O_6S \cdot 1.15CF_3COOH \cdot 0.65H_2O$: C, 47.14; H, 6.15; N, 12.08; F, 9.42; S, 4.61. Found: C, 47.16; H, 5.96; N, 11.74; F, 9.48; S, 4.60.

$[\alpha]_D = +84°$ (c=0.5, $CH_3OH$)

EXAMPLE 10

N-[[[1-Amino(hydroxyimino)methyl]-4-piperidinyl]-methyl]-1-[N-[carboxymethyl]-D-phenylalanyl]-L-prolinamide

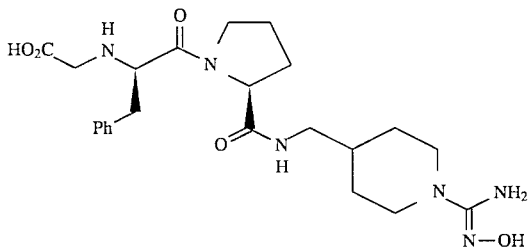

A. N-[(1,1-Dimethylethoxy)carbonyl]-4-piperidinyl]methyl]-1-[N-[[[benzyloxy]-carbonyl]methyl]-D-phenylalanyl]-L-prolinamide

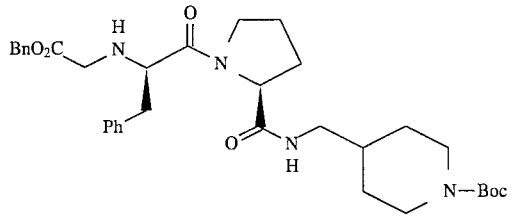

To a solution of Example 1, Part E compound (2.50 g, 5.05 mmol) in dry $CH_2Cl_2$ cooled at 0° C. was added N, N-diisopropylethylamine (5.30 ml, 30.3 mmol), followed by benzyl 2-bromoacetate (1.12 ml, 7.07 mmol). The mixture was stirred at ambient temperature for 5.0 hrs, diluted with $CH_2Cl_2$, washed with water, brine and dried over anhydrous $Na_2SO_4$. Purification by flash chromatography afforded 2.21 g of Part A compound, as a white foam.

B. N-[(1,1-Dimethylethoxy)carbonyl]-4-piperidinyl]methyl]-1-[N-[[[benzyloxy]-carbonyl]methyl]-1-[N-benzyloxycarbonyl]-D-phenylalanyl]-L-prolinamide

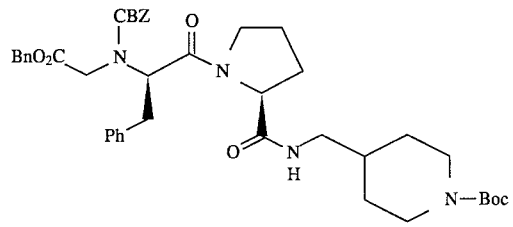

To the solution of Part B compound (1.32 g, 2.17 mmol) in 5 ml of anhydrous DMF cooled at 0° C. was added N, N-diisopropylethylamine (0.94 ml, 5.42 mmol), followed by benzyl chloroformate (0.46 ml, 3.25 mmol). The mixture was stirred at 0° C. for 1.0 hr, diluted with $CH_2Cl_2$, washed with water, brine and dried over anhydrous $Na_2SO_4$. Purification by flash chromatography afforded 1.58 g (98%) of the Part B compound.

C. N-[[[1-Amino(hydroxyimino)methyl]-4-piperidinyl]methyl]-1-[N-[carboxymethyl]-D-phenylalanyl]-L-prolinamide

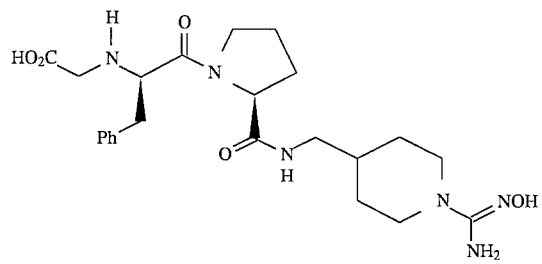

To the solution of Part B compound (1.58 g, 2.13 mmol) in 10 ml of dry $CH_2Cl_2$ at 0° C. was added 10 ml of trifluoroacetic acid dropwise via an additional funnel. The mixture was stirred at 0° C. for 1.0 hr and at room temperature for 1.0 hr. Concentration in vacuo followed by azeotropic evaporation with $CH_2Cl_2$-heptane gave 1.97 g of the TFA salt of the piperidinyl amine as a colorless oil. This material was used directly in the next reaction.

To the mixture of crude TFA salt of amine (1.97 g, 2.13 mmol) and anhydrous sodium acetate (1.05 g, 12.78 mmol) in 17 ml of anhydrous MeOH was added solid cyanogen bromide (338 mg, 3.20 mmol) portionwise. The mixture was stirred at room temperature for 2.0 hrs, concentrated, and the residue taken into $CH_2Cl_2$-water. The organic layer was separated and the aqueous layer was extracted once with $CH_2Cl_2$. The combined organic layers were washed with brine and dried over anhydrous $Na_2SO_4$ to give 1.26 g (91% crude) of the N-cyanamide intermediate as a white foam. This material was used directly in the next reaction.

To the mixture of N-cyanamide benzyl ester (987 mg, 1.48 mmol) in 4 ml of 1:1 THF-water was added $LiOH.H_2O$ (153 mg, 1.78 mmol). The mixture was stirred at room temperature overnight. 0.1N HCl was added at 0° C. until pH =2.5, the mixture was extracted with EtOAc, and the combined organic extracts dried over anhydrous $Na_2SO_4$ to give 1.01 g of the free acid N-cyanamide as a white foam. This material was used directly in the next reaction.

A mixture of hydroxylamine hydrochloride (1.03 g, 14.8 mmol) and anhydrous sodium carbonate (784 mg, 7.4 mmol) in 3.7 ml of anhydrous MeOH was stirred vigorously for 1.0 hr. The solid was removed by filtration through a pad of Celite, the filtrate was added to 1.01 g (1.48 mmol) of crude N-cyanamide, and the reaction mixture was stirred overnight at room temperature. Concentration in vacuo afforded 1.42 g of crude hydroxyguanidine which was taken into a mixture of MeOH (10 ml) and glacial acetic acid (6 ml). To this mixture was added 250 mg of 20% $Pd(OH)_2$, and the mixture was hydrogenated at one atmosphere for 5.0 hrs. The palladium catalyst was removed by filtration, the filtrate concentrated and the product purified to give 220 mg of the title compound.

Following the procedures of Examples 1 to 10, the following examples of compounds of the invention may be prepared.

TABLE
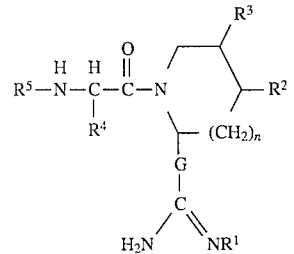
| Example No. | R⁵ | R⁴ | R³ | R² | n | G | R¹ |
|---|---|---|---|---|---|---|---|
| 11 | $C_2H_5SO_2-$ | $CH_2OCH_2Ph(s)$ | H | $CH_3$ | 1 | 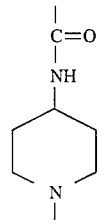 | $NH_2$ |
| 12 | $C_6H_5SO_2-$ | H | OH | H | 0 | 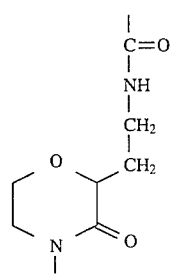 | OH |
| 13 | 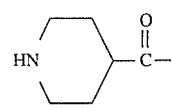 | $-CH_2C_6H_5(R)$ | $OCH_3$ | $CH_3$ | 0 | 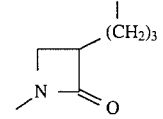 | $OC_2H_5$ |
| 14 | 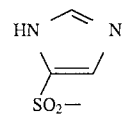 | $-CH_2C_6H_5(R)$ | $CH_3$ | H | 0 | 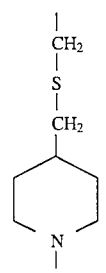 | $NH_2$ |
| 15 | 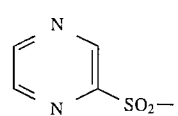 | $-CH_2CH_2CONH_2(S)$ | H | H | 1 | 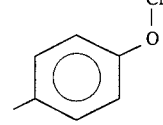 | $NHCH_3$ |

TABLE-continued

| Example No. | R⁵ | R⁴ | R³ | R² | n | G | R¹ |
|---|---|---|---|---|---|---|---|
| 16 | C₆H₅—CO— | —CH₂CH₂CONH₂(R) | H | CH₃ | 1 | 4-methylcyclohexyl-SO₂-CH₂- | NO₂ |
| 17 | 4-pyridyl-CO— | —CH(OH)CH₃(S-Thr) | —CHCH₂CH₂CH— | | 0 | 4-methylbenzamido-CH₂- linked via NH | CN |
| 18 | oxazol-5-yl-O₂C— | CH(OH)CH₃(S-alloThr) | CH₃ | H | 1 | N-methyl-2-oxopyrrolidin-3-yl-carboxamido-CH₂- | OH |
| 19 | thiazol-4-yl-CO— | 3-ethylindol-2-yl (R) | SCH₃ | CH₃ | 1 | 1-methylpiperidin-3-yl-NH-CO- | OCH₃ |
| 20 | quinolin-6-yl-SO₂— | —CH₂CH₂CO₂H(R) | H | CH₃ | 0 | azetidin-3-yl-S-(CH₂)₄-NH-C(=O)- | NH₂ |

TABLE-continued
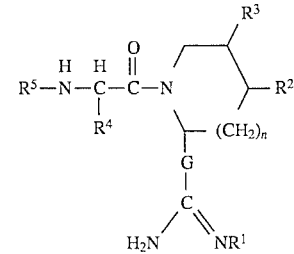
| Example No. | R⁵ | R⁴ | R³ | R² | n | G | R¹ |
|---|---|---|---|---|---|---|---|
| 21 | H | CH₂OCH₂Ph(R) | H | H | 1 |  | N(CH₃)₂ |
| 22 | C₆H₅CH₂O₂C— | CH₂CH₂Ph(S) | H | H | 1 | 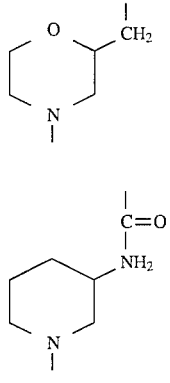 | NO₂ |
| 23 | 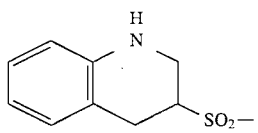 | 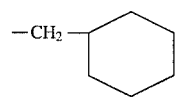 | H | H | 1 | 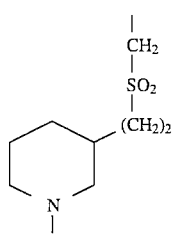 | OH |

TABLE

| Example No. | R⁵ | R⁴ | R³ | R² | n | G | R¹ |
|---|---|---|---|---|---|---|---|
| 24 | $C_2H_5O_2C-CH_2-$ | $CH_2OCH_2Ph(S)$ | H | $CH_3$ | 1 | 1-methylpiperidin-4-yl-NH-C(=O)- | $NH_2$ |
| 25 | $CH_3OO_2C-CH_2-$ | H | OH | H | 0 | (1-methyl-3-oxomorpholin-2-yl)-CH₂-CH₂-NH-C(=O)- | OH |
| 26 | $CH_3O_2C-(CH_2)_2-$ | $-CH_2C_6H_5(R)$ | $OCH_3$ | $CH_3$ | 0 | (1-methyl-2-oxoazetidin-3-yl)-(CH₂)₃-NH-C(=O)- | $OC_2H_5$ |
| 27 | $HO_2C-C_6H_4-CH_2-$ | $-CH_2C_6H_5(R)$ | $CH_3$ | H | 0 | (1-methylpiperidin-4-yl)-CH₂-S-CH₂- | $NH_2$ |
| 28 | $HO_2C-C_6H_4-$ | $-CH_2CH_2CONH_2(S)$ | H | H | 1 | (4-methylphenoxy)-CH₂- | $NHCH_3$ |

TABLE-continued

| # | Col1 | Col2 | Col3 | Col4 | Col5 | Col6 | Col7 |
|---|---|---|---|---|---|---|---|
| 29 | C₂H₅O₂C—⟨C₆H₄⟩—(CH₂)₂— | —CH₂CH₂CONH₂(R) | H | CH₃ | 1 | [4-methylcyclohexyl-SO₂-CH₂-] | NO₂ |
| 30 | C₂H₅—O₂C—CH₂— | —CH(OH)CH₃(S-Thr) | —CHCH₂CH₂CH— | | 0 | [4-methylbenzamido-CH₂- with CN] | CN |
| 31 | C₆H₅O₂C—⟨C₆H₄⟩—CH₂— | CH(OH)CH₃(S-alloThr) | CH₃ | H | 1 | [N-methyl-2-oxopyrrolidin-3-yl-CO-NH-CH₂-] | OH |
| 32 | 3-pyridyl-O₂C—CH₂— | 3-ethylindol-2-yl (R) | SCH₃ | CH₃ | 1 | [1-methylpiperidin-3-yl-NH-CO-] | OCH₃ |
| 33 | quinolin-6-yl-O₂C—CH₂— | —CH₂CH₂CO₂H(R) | H | CH₃ | 0 | [1-methylazetidin-3-yl-S-(CH₂)₄-NH-C(=O)-] | NH₂ |
| 34 | piperidin-4-yl-O₂C—CH₂— | CH₂OCH₂Ph(R) | H | H | 1 | [1-methylmorpholin-2-yl-CH₂-O-CH₂-] | N(CH₃)₂ |
| 35 | C₆H₅CH₂O₂C—(CH₂)₃— | CH₂CH₂Ph(S) | H | H | 1 | [1-methylpiperidin-3-yl-NH-C(=O)-] | NO₂ |

TABLE-continued

| 36 | [1,2,3,4-tetrahydroquinolin-3-yl O₂C-CH₂-] | -CH₂-[cyclohexyl] | H | H | 1 | [1-methylpiperidin-3-yl-(CH₂)₂-SO₂-CH₂-] OH |

$$R^5-N\overset{H}{\underset{(CH_2)_s}{-}}\overset{H}{\underset{\underset{C}{NR}}{C}}\overset{O}{\underset{\parallel}{-}}C-N\overset{R^3}{\underset{\underset{R^9}{(CH_2)_n}}{-}}R^2$$

$$H_2N-C=NR^1$$

| Example No. | R⁵ | R⁹ | s | R³ | R² | n | R | R¹ |
|---|---|---|---|---|---|---|---|---|
| 37 | CBZ | CO₂CH₃ | 0 | H | CH₃ | 1 | H | CN |
| 38 | CH₃O₂C—CH₂— | CO₂C₂H₅ | 1 | OH | H | 0 | CH₃ | OH |
| 39 | C₆H₅CO | CO₂C₃H₇ | 2 | OCH₃ | CH₃ | 0 | H | NH₂ |
| 40 | [imidazol-4-yl-SO₂-] | H | 3 | CH₃ | CH₃ | 1 | H | CN |
| 41 | [4-HO₂C-C₆H₄-] | H | 0 | H | H | 1 | CH₃ | OH |
| 42 | C₆H₅—CH₂CO— | H | 1 | H | CH₃ | 1 | H | OH |
| 43 | [pyridin-4-yl-CO—] | CO₂CH₃ | 2 | —CHCH₂CH₂CH— | | 0 | C₃H₇ | NH₂ |
| 44 | [oxazol-4-yl-O₂C—] | CO₂C₂H₅ | 3 | CH₃ | H | 1 | CH₃ | N(CH₃)₂ |
| 45 | [thiazol-4-yl-O₂C—CH₂—] | H | 0 | SCH₃ | CH₃ | 1 | H | NO₂ |
| 46 | [quinolin-6-yl-SO₂—] | CO₂C₃H₇ | 1 | H | CH₃ | 0 | H | OH |

TABLE-continued $$R^{5'}-NH-\underset{R^{4'}}{\underset{|}{C}}H-\underset{O}{\overset{\|}{C}}-NH-\underset{NH-C(=O)-(CH_2)_p-N(R)-C(NH_2)=NR^1}{\underset{|}{C}}H-R^8$$

| Example No. | R5' | R4' | R8 | R | R1 | p |
|---|---|---|---|---|---|---|
| 47 | C6H5—CH2—CH(CH3)— | CH2OH(S) | —CH2-cyclohexyl | CH3 | CN | 1 |
| 48 | CH3—(CH2)2—CH(CO2H)— | H | —(CH2)2CO2H | H | OH | 0 |
| 49 | C6H5—CH2—CH(CONHCH3)— | —CH2C6H5(R) | C6H5 | C2H5 | NH2 | 0 |
| 50 | piperidin-1-yl—CH2—CH(cyclohexyl)— | CH2OCH2Ph(R) | —CH2-(4-NO2-C6H4) | H | CN | 1 |
| 51 | C4H9—CH2—CH2— | CH2CH2Ph(S) | CO2H | C2H5 | OH | 1 |
| 52 | pyridin-1-yl—CH2—CH(CO2CH3)— | —CH2-cyclohexyl | 4-methylpyridin-yl | H | OCH3 | 2 |

What is claimed is:

1. A compound having the formula

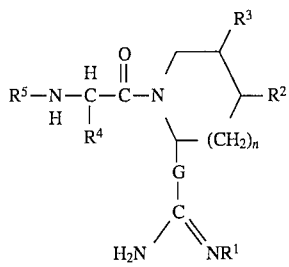

wherein n is 0, 1 or 2;

R$^1$ is hydroxyl, alkoxy, amino, or aminoalkyl;

R$^2$ and R$^3$ are independently hydrogen, lower alkyl, cycloalkyl, aryl, hydroxy, alkoxy, oxo, thioketal, thioalkyl, thioaryl, amino or alkylamino;

R$^4$ is hydrogen, hydroxyalkyl, hydroxy(alkyl)alkyl, aminoalkyl, alkyl, cycloalkyl, aryl, arylalkyl, alkenyl, alkynyl, amidoalkyl, arylalkoxyalkyl or an amino acid side chain, either protected or unprotected;

R$^5$ is

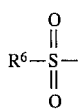 (1)

where R$^6$ is alkyl of from 1 to 18 carbons, aryl, arylalkyl, cycloheteroalkyl, heteroaryl, quinolinyl or tetrahydroquinolinyl; or R$^5$ is (2) hydrogen,

CO$_2$R$^7$, CONHR$^7$, R$^{7'}$O$_2$C-alkyl-,

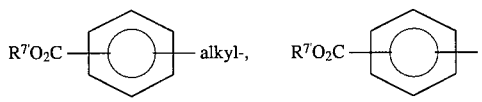

wherein R$^7$ is lower alkyl, aryl, arylalkyl, cycloheteroalkyl or heteroaryl; and R$^{7'}$ is hydrogen, lower alkyl, aryl, arylalkyl, cycloheteroalkyl or heteroalkyl;

G is

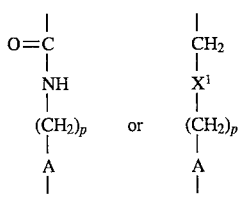

wherein p is 0, 1 or 2, and is connected to

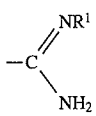

A is an azacyclo-alkyl ring of 3 to 7 carbons in the ring or an azacycloheteroalkyl ring of 4 to 6 carbons in the ring each of the structure

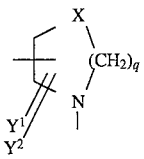

where X is CH$_2$, O or S;

q is 0, 1, 2, 3 or 4, provided that q is 0, 1, 2, 3 or 4 if X is CH$_2$ and q is 2, 3 or 4 if X is O or S;

Y$^1$ and Y$^2$ are independently H, lower alkyl, halo or oxo;

provided that where X is O or S, A is azacycloheteroalkyl, then there must be at least a 2-carbon chain between X and any N atom in the ring or outside the ring;

x$^1$ is NHCO, S, SO, SO2 or O, wherein the term "aryl" by itself or as part of another group refers to a monocyclic or bicyclic aromatic group containing from 6 to 10 carbons in the ring portion;

the term "heteroaryl" as employed herein refers to a 5- to 12-membered aromatic ring which includes 1 or 2 hetero atoms which are N, O or S, said heteroaryl being optional fused to a phenyl ring;

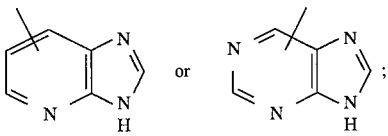

the term "cycloheteroaryl" by itself or as part of another group refers to a 5-, 6- or 7-membered saturated ring which includes 1 or 2 hetero atoms which are N, O or S, or a pharmaceutically acceptable salt thereof.

2. The compound as defined in claim 1 having the formula

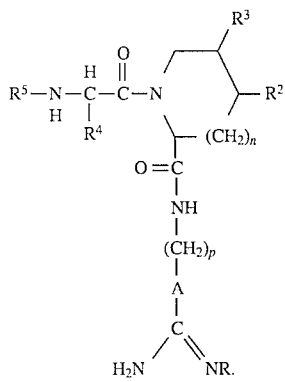

3. The compound as defined in claim 1 having the formula

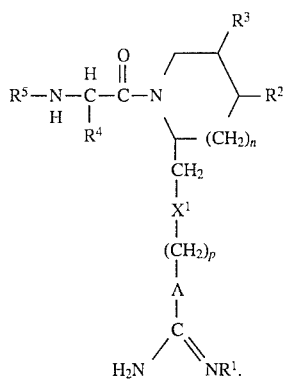

4. The compound as defined in claim 1 having the formula

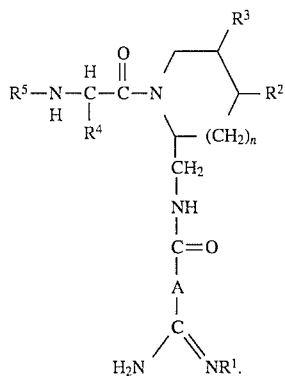

5. The compound as defined in claim 1 wherein $R^1$ is OH, NHR wherein R is H or lower alkyl, or Oalkyl.

6. The compound as defined in claim 1 wherein $R^5$ is

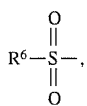

or $HO_2Calkyl-$,
$R^4$ is arylalkyl or hydroxyalkyl, n is O, $R^2$ and $R^3$ are each H, G is

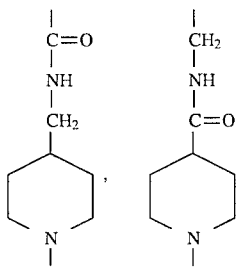

and $R^1$ is OH, NHR wherein R is H or lower alkyl, or Oalkyl.

7. The compound as defined in claim 1 which is

N-[[1-[(hydroxyamino)iminomethyl]-4-piperidinyl]methyl]-1-[N-[(phenylmethyl)sulfonyl]-D-phenylalanyl]-L-prolinamide including its trifluoroacetate salt;

N-[[1-[(hydroxyamino)iminomethyl]-4-piperidinyl]-methyl]-1-[N-[methylsulfonyl]-D-phenylalanyl]-L-prolinamide;

N-[[1-[(methoxyamino)iminomethyl]-4-piperidinyl]methyl]-1-[N-[(methyl)sulfonyl]-D-phenylalanyl]-L-prolinamide;

1S[2R* (3R*)]]-N-[2-[2[[[[1-((hydroxyamino)-iminomethyl))- 3-piperidinyl]carbonyl]amino]methyl]-1-pyrrolidinyl]-1-(hydroxymethyl)-2-oxoethyl]-2-naphthalene sulfonamide;

or

N-[[[1-amino(hydroxyimino)methyl]-4-piperidinyl]methyl]-1-[N-[carboxymethyl]-D-phenyl-alanyl]-L-prolinamide, or a pharmaceutically acceptable salt thereof.

8. The compounds as defined in claim 1 which is N-[[[1-amino(hydroxyimino)methyl]-4-piperidinyl] -methyl]-1-[N-[carboxymethyl]-D-phenylalanyl]-L-prolinamide or a pharmaceutically acceptable salt thereof.

9. A method of inhibiting or preventing formation of blood clots, which comprises administering to a patient in need of treatment a therapeutically effective amount of a compound as defined in claim 1.

10. A pharmaceutical composition comprising a compound as defined in claim 1 and a pharmaceutically acceptable carrier thereof.

* * * * *